United States Patent
Isaac et al.

(10) Patent No.: US 11,505,539 B2
(45) Date of Patent: Nov. 22, 2022

(54) DEUTERATED COMPOUNDS AS INHIBITORS OF THE BCL6 BTB DOMAIN PROTEIN-PROTEIN INTERACTION AND/OR AS BCL6 DEGRADERS

(71) Applicant: Ontario Institute for Cancer Research (OICR), Toronto (CA)

(72) Inventors: Methvin Isaac, Brampton (CA); Anh My Chau, Toronto (CA); Ahmed Mamai, Mississauga (CA)

(73) Assignee: Ontario Institute for Cancer Research (OICR), Toronto (CA)

( * ) Notice: Subject to any disclaimer, the term of this patent is extended or adjusted under 35 U.S.C. 154(b) by 38 days.

(21) Appl. No.: 16/955,998

(22) PCT Filed: Dec. 21, 2018

(86) PCT No.: PCT/CA2018/051642
§ 371 (c)(1),
(2) Date: Jun. 19, 2020

(87) PCT Pub. No.: WO2019/119144
PCT Pub. Date: Jun. 27, 2019

(65) Prior Publication Data
US 2020/0308147 A1 Oct. 1, 2020

Related U.S. Application Data

(60) Provisional application No. 62/609,394, filed on Dec. 22, 2017.

(51) Int. Cl.
 C07D 401/14 (2006.01)
 A61K 31/506 (2006.01)
 A61P 35/02 (2006.01)
 A61K 45/06 (2006.01)

(52) U.S. Cl.
 CPC ............ *C07D 401/14* (2013.01); *A61P 35/02* (2018.01); *A61K 45/06* (2013.01); *C07B 2200/05* (2013.01)

(58) Field of Classification Search
 CPC ...... C07D 401/14; A61K 31/506; A61P 35/00
 USPC .......................................... 544/324; 514/275
 See application file for complete search history.

(56) References Cited

FOREIGN PATENT DOCUMENTS

WO  2018108704 A1  6/2018
WO  2021102283 A1  5/2021

OTHER PUBLICATIONS

Kerres, N. et al.: Chemically induced degradation of the oncogenic transcription factor BCL6. Cell Reports, vol. 20, pp. 2860-2875, 2017.*
International Search Report and Written Opinion of corresponding International Applicaiton No. PCT/CA2018/051642 dated Feb. 28, 2019, 9 pages.
Kerres et al., Chemically Induced Degradation of the Oncogenic Transcription Factor BCL6. Cell Reports, Sep. 2017, vol. 20, pp. 2860-2875.
Extended European Search Report of corresponding EP Patent Application No. 18890560.8 dated Apr. 15, 2021, 8 pages.
Baba S. et al, "Studies on drug metabolism by use of isotopes. 23. Metabolic study of 1-butyryl-4-cinnamylpiperazine in the rat during development of tolerance by using two kinds of deuterium-labeled forms", J. Med. Chem. 1978,vol. 21(6), pp. 525-529.
Slabicki, Mikolaj; Yoon, Hojong; Koeppel, Jonas; Nitsch, Lena; Roy Burman, Shourya S.; Di Genua, Cristina; Donovan, Katherine A.; Sperling, Adam S.; Hunkeler, Moritz; Tsai, Jonathan M.; et al Small-molecule-induced polymerization triggers degradation of BCL6; Nature (London, United Kingdom) (2020), 588(7836), 164-168.
Rana, Sandeep; Natarajan, Amarnath, "Small molecule induced polymerization of BCL6 facilitates SIAH1 mediated degradation", Signal Transduction and Targeted Therapy (2021), 6(1), 142.
Nitsch Lena; Jensen Patrizia; Koeppel Jonas; Frohling Stefan; Slabicki Mikolaj; Yoon Hojong; Slabicki Mikolaj; Yoon Hojong; Slabicki Mikolaj; Yoon Hojong; et al "BTBBCL6 dimers as building blocks for reversible drug-induced protein oligomerization", Cell Reports Methods (2022), 2(4), 100193.

* cited by examiner

*Primary Examiner* — Charanjit Aulakh
(74) *Attorney, Agent, or Firm* — Bereskin & Parr LLP/S.E.N.C.R.L, s.r.l.; Sandra Marone

(57) ABSTRACT

The present application relates to compounds of Formula I (I) or pharmaceutically acceptable salts, solvates and/or prodrugs thereof, to compositions comprising these compounds or pharmaceutically acceptable salts, solvates and/or prodrugs thereof, and various uses in the treatment of diseases, disorders or conditions that are treatable by inhibiting interactions with BCL6 BTB and/or by degrading BCL6, such as cancer.

16 Claims, 1 Drawing Sheet
Specification includes a Sequence Listing.

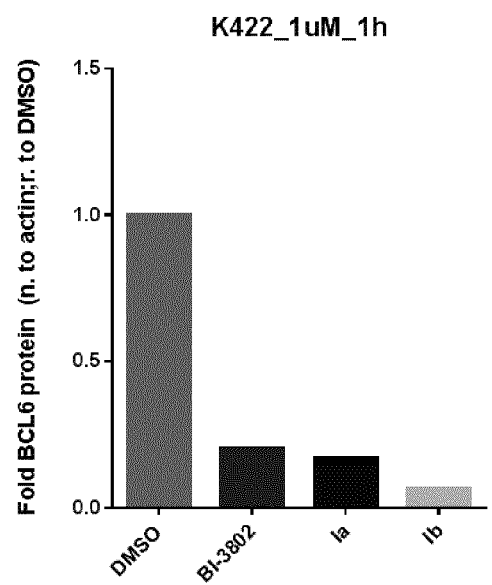

US 11,505,539 B2

DEUTERATED COMPOUNDS AS INHIBITORS OF THE BCL6 BTB DOMAIN PROTEIN-PROTEIN INTERACTION AND/OR AS BCL6 DEGRADERS

CROSS-REFERENCE TO RELATED APPLICATIONS

This application is a National Stage of co-pending International Application No. PCT/CA2018/051642 filed on Dec. 21, 2018 which claims the benefit of priority from U.S. Provisional Patent Application Ser. No. 62/609,394, filed on Dec. 22, 2017, the contents of both of which are incorporated herein by reference in their entirety.

INCORPORATION OF SEQUENCE LISTING

A computer readable form of the Sequence Listing "25308-P54934US01_SequenceListing.txt" (4,096 bytes), submitted via EFS-WEB and created on Oct. 2, 2020, is herein incorporated by reference.

FIELD

The present application relates to novel quinolone compounds, to processes for their preparation, to compositions comprising them, and to their use in therapy. More particularly, it relates to deuterated compounds useful in the treatment of diseases, disorders or conditions treatable by inhibiting or blocking the interaction of BCL6 BTB domain with its binding partners and/or by degrading BCL6.

BACKGROUND

BCL6 (B Cell Lymphoma 6) is a member of the BTB/POZ (bric-á-brac, tramtrack, broad complex/pox virus zinc finger) family of transcription factors. The BCL6 gene was initially cloned by several groups in 1993 from a translocation occurring on chromosome 3q27 in diffuse large B-cell lymphoma (DLBCL) [*Histol Histopathol* 2004, 19:637-650]. Targeted disruption of the BCL6 gene revealed that BCL6 during normal B-cell development is a master regulator of antibody affinity maturation in germinal centers (GCs) [*Nat Rev Immunol* 2008, 8:22-33]. BCL6 is almost universally expressed in GC-derived B-cell lymphomas, including diffuse large B-cell lymphoma (DLBCL) and follicular lymphomas (FLs), regardless of translocations.

In normal lymphoid biology, BCL6 is required for naïve B cells to form GCs which are cellular compartments dedicated to the affinity maturation of antibodies. The GC is the site of two key molecular processes unique to B-cells: somatic hypermutation (SHM) and class switching recombination (CSR) [*Trends Biochem Sci* 2003, 28: 305-312]. Upon antigen-induced B-cell activation, B-cells proliferate and differentiate into either centroblasts or plasma cells [*Annu Rev Immunol* 1994 12: 117-139]. The centroblasts go through the dark zone of the GC where they rapidly proliferate, differentiate and revise their antigen receptors via SHM and CSR [*Cell* 1991 67: 1121-9; *Nature* 1991 354: 389-92; *Cell* 1981 27: 573-581]. SHM modulates the affinity of the antibodies to a specific antigen and, while not wishing to be limited by theory, it is believed that the mistargeting of SHM can result in the translocation of oncogenes.

BCL6 is a transcriptional repressor that reduces mRNA expression of its target genes by regulating survival and differentiation via distinct corepressor complexes [*Proc Natl Acad Sci USA*, 2007. 104(9): 3207-12; *Blood* 2007. 110(6): 2067-74; *Biochem Biophys Res Commun*, 2003. 300(2): 391-6]. BCL6 has six zinc fingers at its carboxyl terminus mediating sequence-specific DNA binding to regulatory sequences [*Nat Immunol*, 2007. 8(7): p. 705-14]. BCL6 binds to DNA as a homo-dimer and recruits, through its N-terminal domain, class I and II histone deacetylase complexes (HDACs) either directly or through corepressor molecules such as SMRT, NCOR1 and BCOR.

Different subsets of target genes appear to be repressed depending on which corepressors are engaged by BCL6 through the BTB domain [*Blood* 2007. 110(6): 2067-74]. The corepressors that bind to the BTB appear to be involved in the regulation of transcription associated with early stages of the GC process. Genome-wide studies indicate that BCL6 may, for example, target as many as 500 genes [*Blood* 2007. 110(6): 2067-74] mainly involved in cell cycle, gene transcription, DNA damage sensing, protein ubiquitylation and chromatin structure modification.

Direct BCL6 repressed target genes include ataxia telangectasia and Rad3 related (ATR), CHK1 checkpoint homolog (*S. pombe*) (CHEK1), tumor protein p53 (TP53) and cyclin dependent kinase inhibitor 1A or p21 (CDKN1A) [*Nat Immunol*, 2007. 8(7): 705-14]. These genes belong to survival pathways involved in DNA damage sensing and checkpoint activation. They are primarily regulated through the SMRT and NCOR corepressors. Both of these corepressors contain a highly conserved 17-residue BCL6 binding domain (BBD) that interacts with the homodimeric BTB domain [*Mol Cell*, 2003. 12(6): 11561-64] forming a promoter-localized protein complex. This complex represses the transcription of target genes such as ATR, TP53 and CDKN1A which in turn attenuates the DNA damage response and promote cell survival.

In addition to its role in survival, BCL6 also regulates differentiation through a specific BCL6 corepressor complex that represses B-lymphocyte-induced maturation protein1 or PRDM1 (BLIMP1), a transcription factor that promotes plasmacytic differentiation [*Cell*, 2004. 119(1): 75-86]. Maturation of GC B cells toward memory B-cells and plasma cells usually requires the down-regulation of BCL6. Such down-regulation of BCL6 function can occur via antigen-induced B cell receptor (BCR) mediated activation that subsequently leads to rapid BCL6 proteasomal degradation [*Genes Dev,* 1998. 12(13): 1953-61]. Alternatively, T-cell-mediated stimulation through the CD40 pathway leads to NF-κB driven induction of interferon regulatory factor 4 (IRF4), a regulator of plasma-cell development [*Science,* 1997. 275(5299): 540-3]. IRF4 leads to the transcriptional repression of BCL6 and to the transactivation of BLIMP1, which drives the regulatory program associated with plasmacytic differentiation and immunoglobulin (Ig) secretion [*Cell.* 1994; 77:297-306].

BCL6 has also been shown to play a role in the regulation of genes involved in the B-T cell interaction by regulating the expression levels of CD80 and CD274 (alias B7-H1, PDL1) [*J Exp Med.* 2003, 198(2):211-2; *Proc Natl Acad Sci USA.* 2009, 106(27):11294-9]. CD80 is expressed on B cells, and its interaction with CD28 is involved in T-cell activation, GC formation, and immunoglobulin class switching [*J Immunol.* 1997, 159(11):5336-44]. The B-T cell interaction is a step toward successful B-cell activation. Another gene for B-cell activation that is regulated by BCL6 is CD69. CD69 (a type II transmembrane glycoprotein) is an early activation marker in lymphocytes and is also a signal transmitter in inflammatory processes [*Life Sci.* 2012, 90(17-18):657-65]. The global BCL6-mediated repression of target genes such as CD69 and CD80 prevent premature activation of B cells during proliferative expansion. A number of other signaling pathways are modulated by BCL6 transcriptional repression. These include multiple interferon-types (e.g. interferon regulatory factor 7 or IRF7) and interleukin receptors as well as STAT (signal transducers and activators of transcription) family members including STAT1, STAT2 and STAT3 [*Adv Immunol.* 2010; 105:193-210; *Blood.* 2010, 115(5):975-84; *Blood* 2008, 111(3):1515-23]. Toll-like-receptor (TLR) signaling is also modulated by BCL6 via regulation of receptor expression (e.g. TLR7) as well as transduction of Toll-derived signals. The TLR pathway has also been shown to play a major role in the development and differentiation of memory B cells [Nature. 2005, 438(7066): 364-8; Adv Exp Med Biol. 2005; 560:11-8; *J Exp Med.* 2007, 204(13):3095-101].

Role of BCL6 in Cancers

The mechanisms that mediate the remodeling of antigen receptors in the GCs involve potentially mutagenic DNA double-strand breaks and suppression of the apoptotic machinery by BCL6. Failure to reactivate apoptosis upon exit from the GC has been established as a mechanism involved in lymphomagenesis, and has been specifically linked to diffuse large B cell lymphoma (DLBCL); an aggressive GC-derived malignancy that accounts for approximately 35% of all non-Hodgkin lymphoma (NHL) cases.

DLBCL is a heterogeneous disease with two major subtypes: the GC B cell-like (GCB) subtype characterized by an expression signature similar to normal GC B cells, and the activated B cell-like (ABC) subtype with gene expression pattern like in vitro BCR stimulation, which has a poorer prognosis [*Nature.* 2000. 403(6769): 503-11]. The most common genetic alterations in DLBCL affect the BCL6 promoter region and involve mutations in the 5' noncoding region and chromosomal translocations. Further experimental evidence that overexpression is sufficient for lymphomagenesis was provided by the production of transgenic mice in which BCL6 was driven by the immunoglobulin heavy chain (IgH) Iμ promoter [*Cancer. Cell.* 2005. 7(5): 445-55]. These mice developed a disease histologically similar to human DLBCL.

Gene rearrangements at 3q27 have been reported in 30-40% of DLBCL with a higher percentage being observed in the ABC subtype [*Oncogene.* 2001. 20(40): 5580-94]. These translocations place an intact BCL6 coding domain under the influence of heterologous promoter regions derived from a variety of alternative partner chromosomes (>20) including the immunoglobulin heavy and light chain genes resulting in deregulated expression of the normal BCL6 protein [*EMBO J.* 1995. 14(24): 6209-17]. In addition, while not wishing to be limited by theory, BCL6 may contribute to lymphomagenesis when its downregulation, which usually occurs after affinity maturation, is disrupted. One proposed mechanism for BCL6 downregulation disruption is the loss of IRF4 binding sites in the BCL6 gene. IRF4 expression is induced by sustained CD40 stimulation of the NF-κB pathway in germinal center cells. IRF4 usually binds to exon 1 and intron 1 of the BCL6 gene and represses BCL6 expression, but chromosome translocations or point mutations introduced during SHM (which commonly target the 5' non-coding promoter region of BCL6) may prevent this repressive effect [*Cancer. Cell.* 2007. 12(3): 280-92]. BCL6 promoter binding and gene repression has also been shown to vary between normal and malignant cells. BCL6 dependency has no correlation to the cell of origin (COO) classification system as dependency occurs in both ABC and GCB cell lines.

Studies have integrated genomic analysis and functional screens to provide a rationale for targeted therapies within defined populations of BCL6 driven DLBCL. Personalizing treatments by identifying patients with oncogenic dependencies via genotyping and specifically targeting the responsible drivers such as BCL6 may be useful for the treatment of DLBCL [*Clin. Cancer. Res,* 2012. 18(17): 4538-48].

Overexpression of BCL6 has been identified as a resistance mechanism arising during the targeted treatment of BCR-ABL1-positive leukemia and suggests a potential therapeutic opportunity to overcome this resistance. The BCR-ABL1 fusion gene is found in nearly all chronic myeloid leukemia (CMLs) and in about 25% of ALLs; the resulting oncogenic protein can be targeted by tyrosine kinase inhibitors (TKIs) such as imatinib, but the acute cellular response reveals protective feedback signaling leading to resistance. BCL6 expression appears to directly influence the response to imatinib as the authors found that modulation of BCL6 levels had the expected effects on the sensitivity of ALL cells to imatinib. A small molecule BTB inhibitor may have utility in, for example, TKI-resistant Ph+ ALL patients, since TKI-resistance develops in most cases of Ph+ ALL. [*Nature,* 2011. 473(7343): 384-388].

CML is induced by the oncogenic BCR-ABL1 tyrosine kinase and can be treated with TKIs. However, if CML patients do not receive life-long TKI treatment, leukemia will eventually recur. —Such recurrence can be attributed to the failure of TKI treatment to eradicate leukemia-initiating cells (LICs). Recent studies demonstrated that forkhead box O (FoxO) transcription factors are critical for maintenance of CML-initiating cells. The BCL6 protooncogene was identified as a downstream effector of FoxO in self-renewal signaling of CML-initiating cells. BCL6 represses Arf and p53 in CML cells and is involved in colony formation and initiation of leukemia [*Curr Opin Immunol,* 2011. 13(2): 134-40]. Inhibition of BCL6 in human CML cells compromises colony formation and leukemia initiation in transplant recipients and selectively eradicates $CD34^+$ $CD38^-$ LICs in patient-derived CML samples. Pharmacological inhibition of BCL6 may therefore eradicate LICs in CML, potentially limiting the duration of TKI treatment in CML patients, and substantially decrease the risk of blast crisis transformation.

X-ray crystallographic studies have shown that the BCL6 BTB domain forms a tight homodimer, and in solution the BCL6 BTB domain also appears to exist exclusively as a dimer, exhibiting a very low dissociation constant [*Mol Cell,* 2003. 12(6): 1551-64]. The BCL6 BTB domain interacts in a mutually exclusive manner with three corepressors: SMRT, NCOR1 and BCOR. Mutations that change the surface of the BCL6 lateral groove (without affecting the overall structure of the domain) no longer bind to the corepressor BBDs, and these mutations abrogate BCL6 BTB domain repressor activity. The above structural features suggest that the BCL6 BTB domain is druggable. Hence, agents that bind to the BCL6 BTB domain and compete for corepressor binding can reverse the repression activities of BCL6. Selective targeting of the BCL6 BTB domain could minimize toxicity compared to complete abrogation of BCL6 function. However, the length and complexity of the interface between the BBD and the BCL6 BTB binding groove are potential barriers toward developing effective small molecule inhibitors. Molecules such as BBD peptides, which contain many polar and charged amino acids, interact with an extended surface of the BCL6 BTB dimer, mostly through hydrogen bonds and multiple Van der Waals contacts. Molecules large enough to fully occupy the lateral groove would be unlikely to readily penetrate cells as demonstrated by the peptide BPI, which has potency in the micromolar range and a short half-life in vivo [*Nat Med,* 2004. 10(12): 1329-35]. Three articles have reported the identification of chemical ligands for the BTB domain of BCL6, for example *J. Med. Chem.* 2017, 60, 4358-4368 and *J. Med. Chem.* 2017, 60, 4386-4402. Further Kerres et al. have recently described a small molecule quinolone-based BCL6 BTB inhibitor, BI-3802 that induces BCL6 degradation (*Cell Reports* 2017, 20, 2860-2875):

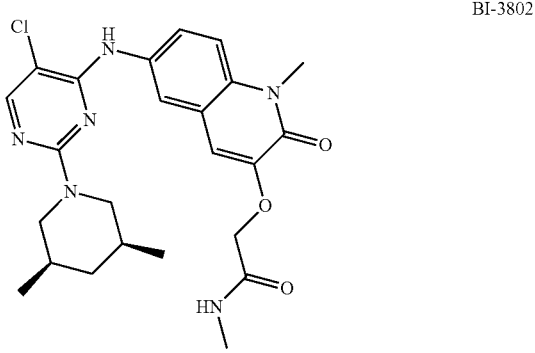 [SMILES: CNC(=O)COc1cc2cc(Nc3nc(N4C[C@H](C)C[C@H](C)C4)ncc3Cl)ccc2n(C)c1=O]

BI-3802

Induced degradation of transcription factors is not unprecedented. Like BCL6, estrogen receptors can be inhibited by antagonists such as tamoxifen that modulate the interaction of the receptor with transcriptional activators. Recently, chemically induced degradation of proteins by small molecules that bridge the target protein to the ubiquitin-dependent degradation machinery has become an emerging field in drug discovery (*Angew. Chem. Int. Ed. Engl.* 2016, 55, 1966-1973; *Pharmacol Ther.* 2017; 174:138-144; *Cell Chemical Biology* 2018, 25, 1-15). The observation that the mere inhibition of the BCL6 BTB domain has milder effects on transcription of repressed genes than the removal of the whole protein is reminiscent of the stronger effects that PROTACs (proteolysis-targeting chimeras) have compared to the parent inhibitors. These observations are in line with reports showing that regions outside of the BTB domain of BCL6 also partake in the transcriptional repression necessary for the physiological function of BCL6 (*Nat. Immunol.* 2014, 14, 380-388; *Proc. Natl. Acad. Sci. USA* 2015, 112, 13324-13329).

Despites its good BCL6 BTB potency and efficacious BCL6 degradation profile, BI-3802 was reported to suffer from poor bioavailability that limits its use in animal studies. Such poor pharmacokinetic profile has been attributed in part to poor metabolism in both mouse and human microsomes.

Considering the challenges generally associated with targeting protein-protein interactions and the current need that exists to treat BCL6 dependent tumor types such as DLBCL, complementary approaches, namely virtual screening, focused library screening and traditional structure activity relationship studies, were used to identify compounds of Formula I which inhibit the BCL6 BTB protein-protein interaction. Furthermore, the molecular features that confer good metabolic and pharmacokinetic characteristic are at times unpredictable. We have identified key structural feature in compounds of Formula I that exhibit improved metabolic properties for the treatment of diseases, disorders or conditions treatable by inhibiting or blocking the interaction of BCL6 BTB domain with its binding partners and/or by degrading BCL6.

One strategy for improving a drug's metabolic properties is deuterium modification. In this strategy one or more hydrogen atoms in a molecule are replaced with deuterium atoms with the aim to slow the CYP-mediated metabolism of a drug or to reduce the formation of undesirable metabolites. Furthermore, deuterium can be used to mitigate chiral center epimerization and prevent the formation of potentially harmful drug racemates. Deuterium is a safe, stable, nonradioactive, inexpensive isotope of hydrogen. Deuterium carbon bonds are stronger than corresponding hydrogen carbon bonds and in select cases, this increased bond strength can positively impact the absorption, distribution, metabolism, and excretion (ADME) properties of a drug. For example, by decreasing the propensity of a molecule for metabolism by certain enzymes, there is a potential for improved drug efficacy, safety, and/or tolerability. At the same time, because the size and shape of deuterium are essentially identical to those of hydrogen, the corresponding deuterated compound is expected to have similar biological potency compared to the original chemical entity that contains only hydrogen.

The effects of deuterium substitution on metabolic stability have been reported for a very small percentage of approved drugs (see, e.g., Blake, M I et al, J Pharm Sci, 1975, 64:367-91; Foster, A B, Adv Drug Res, 1985, 14:1-40 ("Foster"); Kushner, D J et al, Can J Physiol Pharmacol, 1999, 79-88; Fisher, M B et al, Curr Opin Drug Discov Devel, 2006, 9:101-09 ("Fisher")). In general, whether or not deuterium modification will affect a compound's metabolic properties is not predictable even when deuterium atoms are incorporated at known sites of metabolism. It is only by preparing and testing the pharmacological properties of a deuterated compound that the affect of deuteration on the rate of metabolism of the compound can be determined (see, for example, Fukuto et al. (J. Med. Chem., 1991, 34, 2871-76)). One reason for this is that many compounds have multiple sites where metabolism is possible. Therefore, the site(s) where deuterium substitution is required and the extent of deuteration necessary to see an effect on metabolism, if any, will be different for each drug.

SUMMARY

Considering the challenges generally associated with targeting protein-protein interactions, and the current need that exists to treat BCL6 dependent tumor types such as DLBCL, complementary approaches, namely virtual screening, focused library screening and traditional structure activity relationship studies, were used to identify compounds of the application which inhibit or block the interaction of the BCL6 BTB domain with its binding partners, such as the SMRT, NCOR2 and BCOR corepressors as well as compounds which are effective BCL6 degraders. In some embodiments, the compounds of the application have improved metabolic properties.

Accordingly, the present application includes a compound of Formula I, or a pharmaceutically acceptable salt, solvate and/or prodrug thereof:

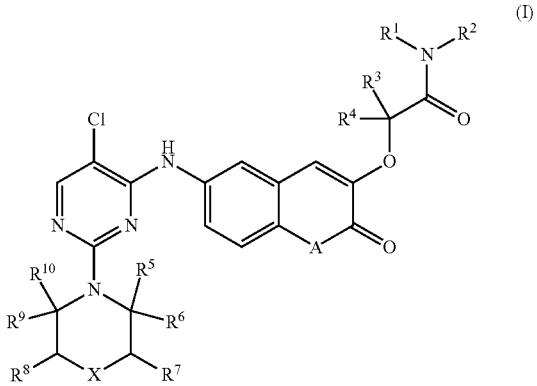

(I)

wherein

A is selected from O and NR$^{11}$;

X is selected from $CH_2$, $CF_2$, $CD_2$, CHF, CDF and CHD;

$R^1$ and $R^2$ are independently selected from H, D, $C_{1-4}$alkyl and deuterium-substituted $C_{1-4}$alkyl;

$R^3$, $R^4$, $R^5$, $R^6$, $R^9$ and $R^{10}$ are independently selected from H and D;

$R^7$ and $R^8$ are independently $CR^{12}R^{13}R^{14}$, $R^{11}$ is selected from H, $C_{1-4}$alkyl and deuterium-substituted $C_{1-4}$alkyl;

$R^{12}$, $R^{13}$ and $R^{14}$ are independently selected from H, D and F; and all alkyl groups are optionally fluoro-substituted and the compound of Formula I comprises at least one D.

The present application also includes a composition comprising one or more compounds of the application and a carrier. In an embodiment, the composition is a pharmaceutical composition comprising one or more compounds of the application and a pharmaceutically acceptable carrier.

In some embodiments, the compounds of the application are used as medicaments. Accordingly, the application also includes a compound of the application for use as a medicament.

The compounds of the application have been shown to inhibit or block BCL6 BTB protein-protein interaction with its binding partners, in particular SMRT/NCOR and BCOR, as well as to promote the degradation of BCL6. Therefore the compounds of the application are useful for treating diseases, disorders or conditions that are treatable by inhibiting interactions with BCL6 BTB and/or by degrading BCL6. Accordingly, the present application also includes a method of treating a disease, disorder or condition that is treatable by inhibiting interactions with BCL6 BTB and/or by degrading BCL6, comprising administering a therapeutically effective amount of one or more compounds of the application to a subject in need thereof.

The present application also includes a use of one or more compounds of the application for treatment of a disease, disorder or condition that is treatable by inhibiting interactions with BCL6 BTB and/or by degrading BCL6, as well as a use of one or more compounds of the application for the preparation of a medicament for treatment of a disease, disorder or condition that is treatable by inhibiting interactions with BCL6 BTB and/or by degrading BCL6. The application further includes one or more compounds of the application for use in treating a disease, disorder or condition that is treatable by inhibiting interactions with BCL6 BTB and/or by degrading BCL6.

In some embodiments, the disease, disorder or condition that is treatable by inhibiting interactions with BCL6 BTB and/or by degrading BCL6, is a neoplastic disorder. In an embodiment, the treatment comprises administration or use of an amount of one or compounds of the application that is effective to ameliorate at least one symptom of the neoplastic disorder, for example, reduced cell proliferation or reduced tumor mass in a subject in need of such treatment.

In some embodiments, the disease, disorder or condition that is treatable by inhibiting interactions with BCL6 BTB and/or by degrading BCL6, is cancer. In some embodiments, the cancer is selected from hematologic cancer, breast cancers, ovarian cancers and glioblastomas. In some embodiments, the cancer is a B-cell lymphoma, such as diffuse large B-cell lymphoma (DLBCL) or follicular lymphomas.

In an embodiment, the disease, disorder or condition that is treatable by inhibiting interactions with BCL6 BTB and/or by degrading BCL6, is a disease, disorder or condition associated with an uncontrolled and/or abnormal cellular activity affected directly or indirectly by the interaction of protein binding partners with the BCL6 BTB binding domain and/or by degradation of BCL6. In another embodiment, the uncontrolled and/or abnormal cellular activity that is affected directly or indirectly by the interaction of protein binding partners with the BCL6 BTB binding domain and/or by degradation of BCL6 is proliferative activity in a cell.

The application also includes a method of inhibiting proliferative activity in a cell, comprising administering an effective amount of one or more compounds of the application to the cell.

In a further embodiment the disease, disorder or condition that is treatable by inhibiting interactions with BCL6 BTB and/or by degrading BCL6, is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

The application additionally provides a process for the preparation of compounds of the application. General and specific processes are discussed in more detail and set forth in the Examples below.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The present application will be described in greater detail with reference to the attached drawings in which:

FIG. 1 is a graph showing the relative BCL6 expression levels after incubation of Karpas422 cells with exemplary compounds of the application and controls for 1 hour.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps.

As used herein, the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds. In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

Unless otherwise indicated, the definitions and embodiments described in this and other sections are intended to be applicable to all embodiments and aspects of the application herein described for which they are suitable as would be understood by a person skilled in the art.

Unless otherwise specified within this application or unless a person skilled in the art would understand otherwise, the nomenclature used in this application generally follows the examples and rules stated in "Nomenclature of Organic Chemistry" (Pergamon Press, 1979), Sections A, B, C, D, E, F, and H. Optionally, a name of a compound may be generated using a chemical naming program: ACD/ChemSketch, Version 5.09/September 2001, Advanced Chemistry Development, Inc., Toronto, Canada.

The term "compound(s) of the application" or "compound(s) of the present application" and the like as used herein refers to a compound of Formula I, and pharmaceutically acceptable salts, solvates and/or prodrugs thereof.

The term "composition(s) of the application" or "composition(s) of the present application" and the like as used herein refers to a composition comprising one or more compounds the application and at least one additional ingredient.

The term "suitable" as used herein means that the selection of the particular compound or conditions would depend on the specific synthetic manipulation to be performed, and the identity of the species to be transformed, but the selection would be well within the skill of a person trained in the art. All method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form are included within the scope of the present application.

The compounds of the present application may further exist in varying polymorphic forms and it is contemplated that any polymorphs which form are included within the scope of the present application.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas).

The term "cell" as used herein refers to a single cell or a plurality of cells and includes a cell either in a cell culture or in a subject.

The term "subject" as used herein includes all members of the animal kingdom including mammals, and suitably refers to humans. Thus the methods and uses of the present application are applicable to both human therapy and veterinary applications.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. Either the mono- or di-acid salts can be formed, and such salts can exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, EGFRaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful so that an ester functionality, if any, elsewhere in a compound is not hydrolyzed. The selection criteria for the appropriate salt will be known to one skilled in the art.

Prodrugs of the compounds of the present application may be, for example, conventional esters formed with available hydroxy, thiol, amino or carboxyl groups. Some common esters which have been utilized as prodrugs are phenyl esters, aliphatic ($C_1$-$C_{24}$) esters, acyloxymethyl esters, carbamates and amino acid esters.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "inert organic solvent" as used herein refers to a solvent that is generally considered as non-reactive with the functional groups that are present in the compounds to be combined together in any given reaction so that it does not interfere with or inhibit the desired synthetic transformation. Organic solvents are typically non-polar and dissolve compounds that are non soluble in aqueous solutions.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-4}$alkyl means an alkyl group having 1, 2, 3 or 4 carbon atoms. All alkyl groups are optionally fluorosubstituted unless otherwise stated.

The term "optionally substituted" refers to groups, structures, or molecules that are either unsubstituted or are substituted with one or more substituents.

The term "fluorosubstituted" refers to the substitution of one or more, including all, hydrogens in a referenced group with fluorine.

The term "deuterium-substituted" refers to the substitution of one or more, including all, hydrogens in a referenced group with deuterium.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas).

The term "atm" as used herein refers to atmosphere.

The term "MS" as used herein refers to mass spectrometry.

The term "aq." As used herein refers to aqueous.

The term "DCM" as used herein refers to dichloromethane.

The term "DIPEA" as used herein refers to N,N-diisopropyl ethylamine.

The term "DMF" as used herein refers to dimethylformamide.

The term "THF" as used herein refers to tetrahydrofuran.

The term "DMSO" as used herein refers to dimethylsulfoxide.

The term "EtOAc" as used herein refers to ethyl acetate.

The term "MeOH" as used herein refers to methanol.

The term "MeCN" or "ACN" as used herein refers to acetonitrile.

The term "HCl" as used herein refers to hydrochloric acid.

The term "TFA" as used herein refers to trifluoroacetic acid.

The term "CV" as used herein refers to column volume.

The term "Hex" as used herein refers to hexanes.

The term "PBS" as used herein refers to phosphate-based buffer.

The term "HBTU" as used herein refers to 2-(1H-benzotriazol-1-yl)-1,1,3,3-tetramethyluronium hexafluorophosphate.

The term "HATU" as used herein refers to 1-[bis(dimethylamino)methylene]-1H-1,2,3-triazolo[4,5-b]pyridinium 3-oxide hexafluorophosphate.

The term "RT" as used herein refers to room temperature.

The term "DIAD" as used herein refers to diisopropyl azodicarboxylate.

The term "TPP" as used herein refers to triphenylphosphine.

The term "TLC" as used herein refers to thin-layer chromatography.

The term "MOM-Cl" as used herein refers to methoxymethyl chloride.

The term "EDC-HCl" as used herein refers to N'-ethylcarbodiimide hydrochloride.

The term "TMEDA" as used herein refers to tetramethylethylenediamine.

The term "PyBOP" as used herein refers to benzotriazol-1-yl-oxytripyrrolidinophosphonium hexafluorophosphate.

The term "TEA" as used herein refers to triethylamine.

The term "mCPBA" as used herein refers to meta-chloroperoxybenzoic acid.

The term "TMSCl" as used herein refers to trimethylsilylchloride.

The term "NBS" as used herein refers to N-bromosuccinimide.

The term "DBAD" as used herein refers to di-tert-butyl azodicarboxylate.

The term "DPPA" as used herein refers to diphenylphosphoryl azide.

The term "NMP" as used herein refers to N-methyl-2-pyrrolidone.

The term "DiPA" as used herein refers to diisopropyl amine.

The term "NCS" as used herein refers to N-chloro succinimide.

The term "PMDTA" as used herein refers to N,N,N',N'',N''-pentamethyldiethylenetriamine.

The term "DIMAP" as used herein refers to 4-Dimethylaminopyridine.

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment.

"Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations. For example, in some embodiments, the compounds of the application may be administered at least once a week. In some embodiments, the compounds may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required. For example, the compounds are administered to the subject in an amount and for duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition treatable by inhibition of interactions with BCL6 BTB, or manifesting a symptom associated with a disease, disorder or condition treatable by inhibition of BCL6 BTB protein-protein interaction.

As used herein, the term "effective amount" or "therapeutically effective amount" means an amount of a compound, or one or more compounds, of the application that is effective, at dosages and for periods of time necessary to achieve the desired result. For example in the context of treating a disease, disorder or condition treatable by inhibition of interactions with BCL6 BTB, an effective amount is an amount that, for example, inhibits interactions with BCL6 BTB, compared to the inhibition without administration of the one or more compounds. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art. The effective amount is one that following treatment therewith manifests as an improvement in or reduction of any disease symptom.

When the disease is cancer, amounts that are effective can cause a reduction in the number, growth rate, size and/or distribution of tumours.

The expression "inhibiting interactions with BCL6 BTB" as used herein refers to inhibiting, blocking and/or disrupting an interaction between a therapeutically relevant binding partner, such as a corepressor protein, with the BCL6 BTB binding domain in a cell, in particular a B-cell. The inhibiting, blocking and/or disrupting causes a therapeutic effect in the cell.

By "inhibiting, blocking and/or disrupting" it is meant any detectable inhibition, block and/or disruption in the presence of a compound compared to otherwise the same conditions, except for in the absence in the compound.

The term "BCL6 BTB" as used herein refers to the bric-á-brac, tramtrack, broad (BTB) domain of B-cell lymphoma 6 (BLC6) which comprises the amino acid sequence disclosed in *Mol. Cell* 2008, 29: 384-391.

The term "SMRT" as used herein refers to a corepressor protein that interacts with BCL6 BTB and this interaction results in the reduction of mRNA expression of target genes. SMRT (Gene ID: 9612) comprises the amino acid sequence disclosed *Proc Natl Acad Sci* 1999, 96: 2639-2644 and *Proc Natl Acad Sci,* 1999 96: 3519-3524.

The term "NCOR" as used herein refers to a corepressor protein that interacts with BCL6 BTB and this interaction results in the reduction of mRNA expression of target genes. NCOR (Gene ID: 9611) comprises the amino acid sequence disclosed in *Proc Natl Acad Sci* 1999, 96: 2639-2644 and *Proc Natl Acad Sci,* 1999 96: 3519-3524.

The term "BCOR" as used herein as used herein refers to a corepressor protein that interacts with BCL6 BTB and this interaction results in the reduction of mRNA expression of target genes. BCOR (Gene ID: 54880) comprises the amino acid sequence disclosed in *Genes Dev.* 2000, 14, 1810-1823.

The term "degrading BCL6" or "degradation of BCL6" as used herein means that the amount of BCL6 protein in a cell in the presence of a compound is less compared to the amount in the absence of a compound, with all other conditions being constant.

The term "administered" as used herein means administration of a therapeutically effective amount of a compound, or one or more compounds, or a composition of the application to a cell either in cell culture or in a subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer).

II. Compounds

The present application includes a compound of Formula I, or a pharmaceutically acceptable salt, solvate and/or prodrug thereof:

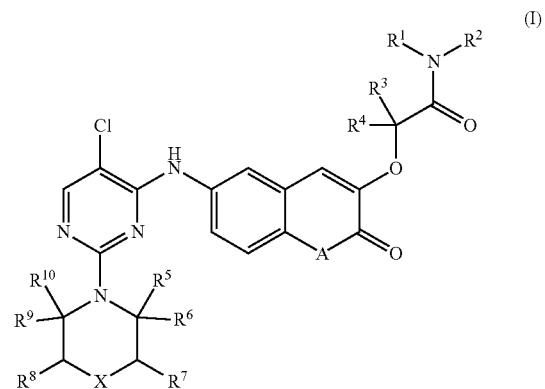

A is selected from O and $NR^{11}$;
X is selected from $CH_2$, $CF_2$, $CD_2$, CHF, CDF and CHD;
$R^1$ and $R^2$ are independently selected from H, D, $C_{1-4}$alkyl and deuterium-substituted $C_{1-4}$alkyl;
$R^3$, $R^4$, $R^5$, $R^6$, $R^9$ and $R^{10}$ are independently selected from H and D;
$R^7$ and $R^8$ are independently $CR^{12}R^{13}R^{14}$,
$R^{11}$ is selected from H, $C_{1-4}$alkyl and deuterium-substituted $C_{1-4}$alkyl;
$R^{12}$, $R^{13}$ and $R^{14}$ are independently selected from H, D and F; and
all alkyl groups are optionally fluoro-substituted and the compound of Formula I comprises at least one D.

In some embodiments, A is $NR^{11}$ and $R^{11}$ is selected from H, $CH_3$ and $CD_3$. In some embodiments, A is $NCH_3$.

In some embodiments, X is selected from $CH_2$, and $CF_2$.

In some embodiments, $R^1$ and $R^2$ are independently selected from $CH_3$ and $CD_3$. In some embodiments, $R^1$ and $R^2$ are the same and are selected from $CH_3$ and $CD_3$.

In some embodiments, $R^3$, $R^4$, $R^5$, $R^6$, $R^9$ and $R^{10}$ are all H. In some embodiments $R^3$, $R^4$, $R^5$, $R^6$, $R^9$ and $R^{10}$ are all D. In some embodiments, $R^3$ and $R^4$ are D and $R^5$, $R^6$, $R^9$ and $R^{10}$ are all H.

In some embodiments, $R^7$ and $R^8$ are the same and are selected from $CH_3$, $CF_3$, $CD_3$ and $CD_2F$.

In some embodiments, the stereochemistry in the compounds of Formula I is as follows:

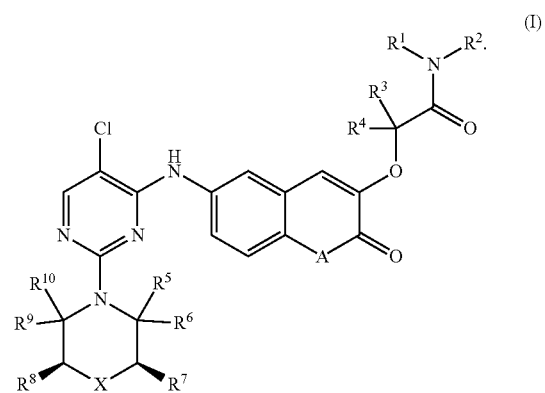

In some embodiments, the compound of Formula I is selected from compound number Ia to Iv, or a pharmaceutically acceptable salt, solvent and/or prodrug thereof:

| No | Structure |
|---|---|
| Ia | (structure) |
| Ib | (structure) |
| Ic | (structure) |
| Ie | (structure) |
| If | (structure) |
| Ig | (structure) |
| Ih | (structure) |
| Ii | (structure) |

-continued
| No | Structure |
|---|---|
| Ij | 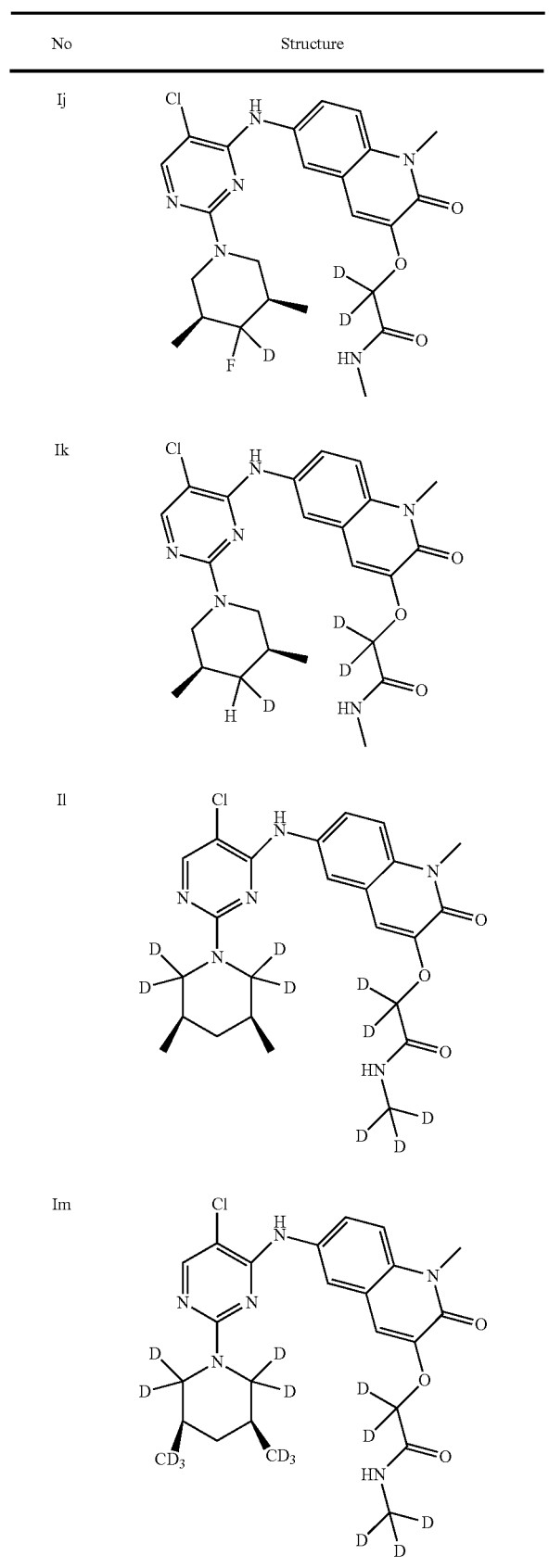 |
| Ik | 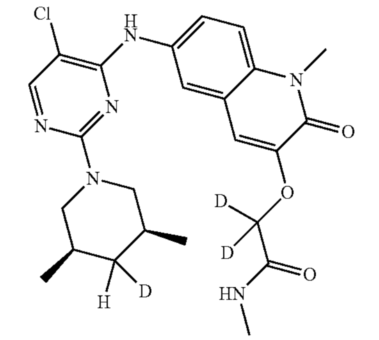 |
| Il | 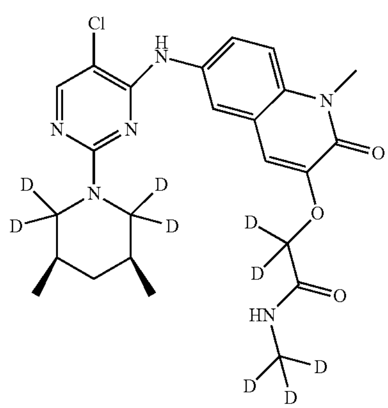 [SMILES: [2H]C([2H])([2H])NC(=O)C([2H])([2H])Oc1cc2cc(Nc3nc(N4C([2H])([2H])[C@H](C)C[C@H](C)C4([2H])[2H])ncc3Cl)ccc2n(C)c1=O] |
| Im | 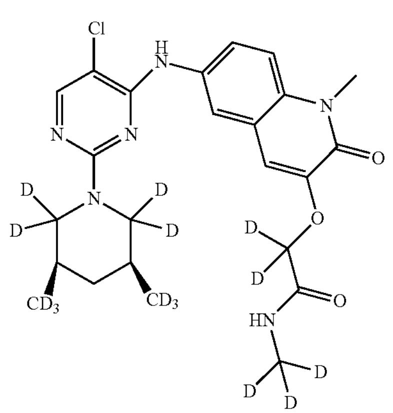 [SMILES: [2H]C([2H])([2H])NC(=O)C([2H])([2H])Oc1cc2cc(Nc3nc(N4C([2H])([2H])[C@@H](C([2H])([2H])[2H])C[C@@H](C([2H])([2H])[2H])C4([2H])[2H])ncc3Cl)ccc2n(C)c1=O] |
-continued
| No | Structure |
|---|---|
| In | 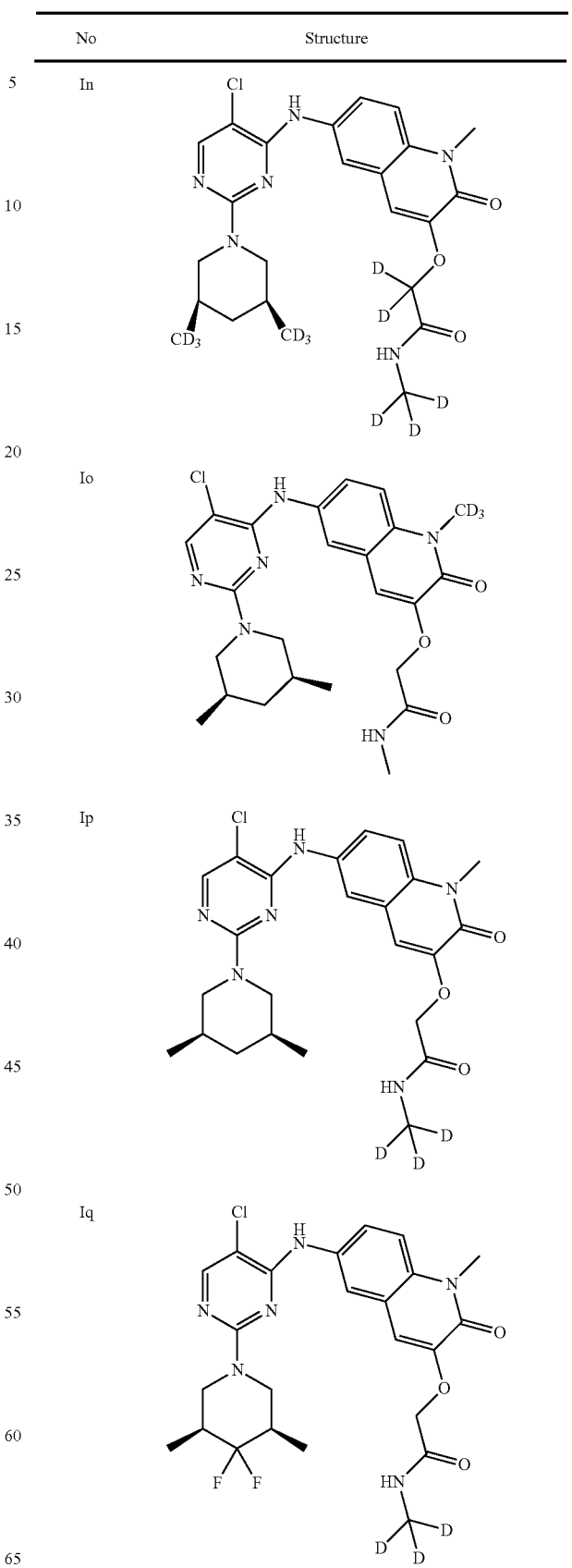 |
| Io | 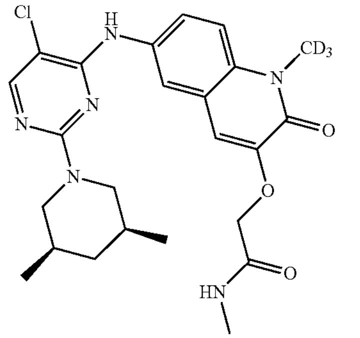 [SMILES: [2H]C([2H])([2H])n1c(=O)c(OCC(=O)NC)cc2cc(Nc3nc(N4C[C@H](C)C[C@H](C)C4)ncc3Cl)ccc21] |
| Ip | 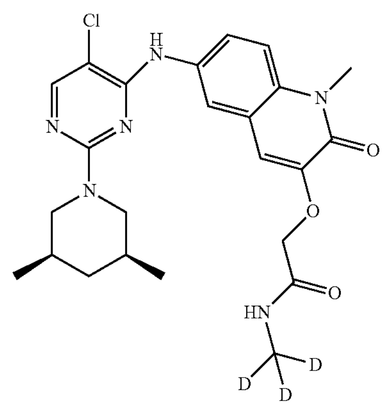 [SMILES: [2H]C([2H])([2H])NC(=O)COc1cc2cc(Nc3nc(N4C[C@H](C)C[C@H](C)C4)ncc3Cl)ccc2n(C)c1=O] |
| Iq | 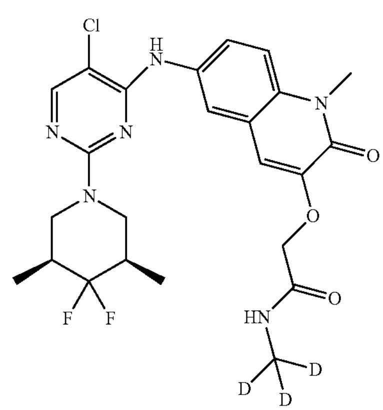 [SMILES: [2H]C([2H])([2H])NC(=O)COc1cc2cc(Nc3nc(N4C[C@@H](C)C(F)(F)[C@@H](C)C4)ncc3Cl)ccc2n(C)c1=O] |

| No | Structure |
|---|---|
| Ir | 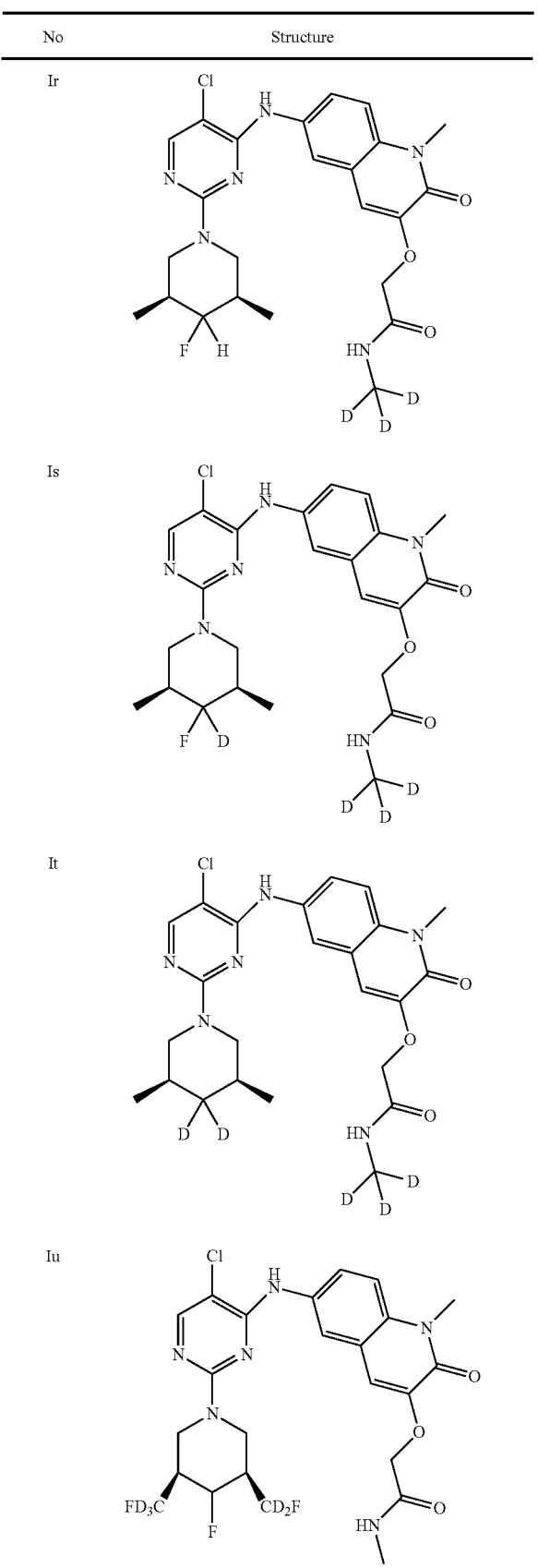 |
| Is | |
| It | |
| Iu | |
| No | Structure |
|---|---|
| Iv | 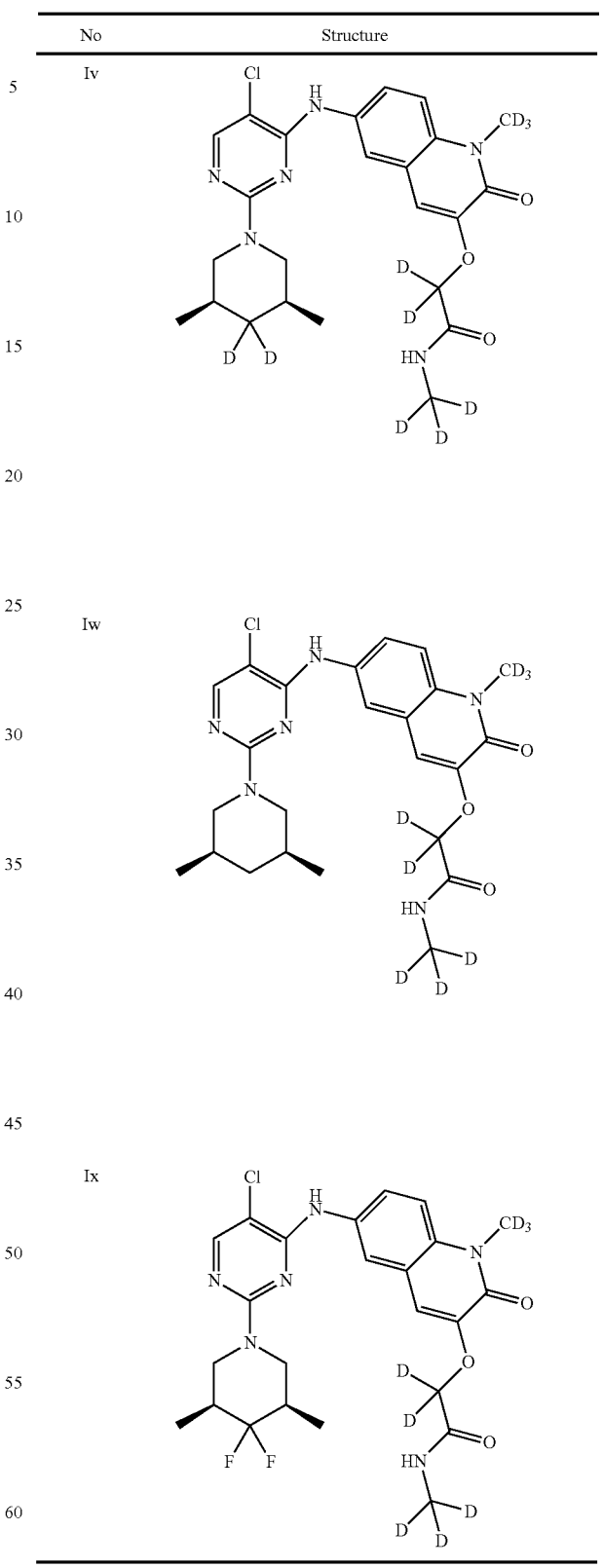 |
| Iw | |
| Ix | |
In some embodiments, the compound of Formula I is selected from compound number Ia, Ib, Ih and Ig or a pharmaceutically acceptable salt, solvent and/or prodrug thereof:

| No | Structure |
|---|---|
| Ia | 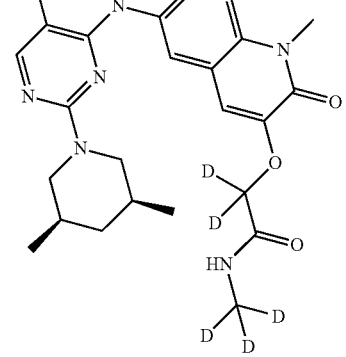 |
| Ib | 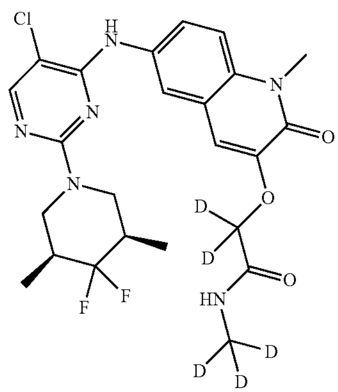 |
| Ih | 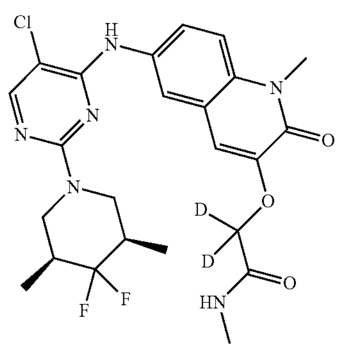 |
| Ig | 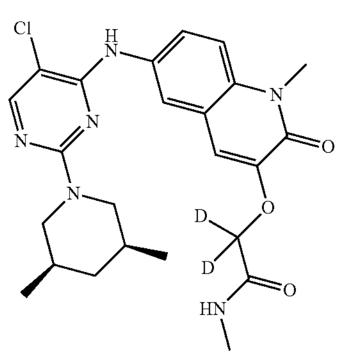 [SMILES: [2H]C([2H])(Oc1cc2cc(Nc3nc(N4C[C@H](C)C[C@H](C)C4)ncc3Cl)ccc2n(C)c1=O)C(=O)NC] |

| No | Structure |
|---|---|
| Ia | 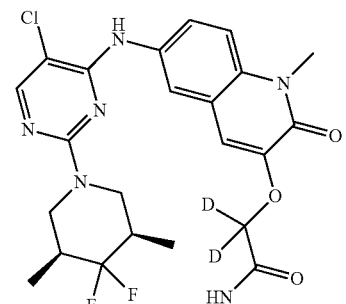 |
| Ib | 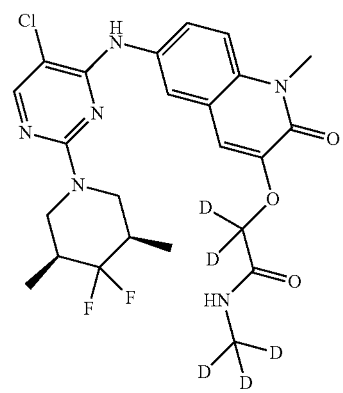 [SMILES: [2H]C([2H])([2H])NC(=O)C([2H])([2H])Oc1cc2cc(Nc3nc(N4C[C@@H](C)C(F)(F)[C@@H](C)C4)ncc3Cl)ccc2n(C)c1=O] |

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier.

The compounds of the application may be administered to a subject in a variety of forms depending on the selected route of administration, as will be understood by those skilled in the art. A compound of the application may be administered, for example, by oral, parenteral, buccal, sublingual, nasal, rectal, patch, pump or transdermal administration and the pharmaceutical compositions formulated accordingly. Administration can be by means of a pump for periodic or continuous delivery.

Parenteral administration includes intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time. Conventional procedures and ingredients for the selection and preparation of suitable compositions are described, for example, in Remington's Pharmaceutical Sciences (2000—20th edition) and in The United States Pharmacopeia: The National Formulary (USP 24 NF19) published in 1999.

In some embodiments, the compound of Formula I is selected from compound number Ia and Ib or a pharmaceutically acceptable salt, solvent and/or prodrug thereof:

A compound of the application may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines. For oral administration in a capsule form, useful carriers or diluents include lactose and dried corn starch.

Liquid preparations for oral administration may take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents may be added. Such liquid preparations for oral administration may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

A compound of the application may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

The compounds of the application may be formulated for parenteral administration by injection, including using conventional catheterization techniques or infusion. Formulations for injection may be presented in unit dosage form, e.g., in ampoules or in multi-dose containers, with an added preservative. The compositions may take such forms as sterile suspensions, solutions or emulsions in oily or aqueous vehicles, and may contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

Compositions for nasal administration may conveniently be formulated as aerosols, drops, gels and powders.

For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of the application including pharmaceutically acceptable salts, solvates and prodrugs thereof are suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient (one or more compounds of the application), and from about 1 wt % to about 99.95 wt % or about 30 wt % to about 99.90 wt % of a pharmaceutically acceptable carrier, all percentages by weight being based on the total composition.

Compounds of the application may be used alone or in combination with other known agents useful for treating diseases, disorders or conditions treatable by inhibiting interactions with BCL6 BTB. When used in combination with other agents useful in treating diseases, disorders or conditions that are treatable by inhibiting interactions with BCL6 BTB, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application (e.g. a compound of Formula I), an additional therapeutic agent, and a pharmaceutically acceptable carrier.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. Dosages will generally be selected to maintain a serum level of compounds of the application from about 0.01 µg/cc to about 1000 µg/cc, or about 0.1 µg/cc to about 100 µg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. Compounds of the application may be administered in a single daily, weekly or monthly dose or the total daily dose may be divided into two, three or four daily doses.

To be clear, in the above, the term "a compound" also includes embodiments wherein one or more compounds are referenced.

III. Methods and Uses

The compounds of the application have been shown to be capable of inhibiting or blocking the interaction of BCL6 BTB binding domain with its corepressor binding partner SMRT/NCOR. The compounds have also been shown to inhibit tumor cell growth, specifically the Karpas-422 cell line. The compounds have also been shown to be degraders of BCL6.

Accordingly, the present application includes a method for inhibiting interactions with BCL6 BTB and/or degrading BCL6, in a cell, either in a biological sample or in a patient, comprising administering an effective amount of one or more compounds of the application to the cell. The application also includes a use of one or more compounds of the application for inhibiting interactions with BCL6 BTB and/or degrading BCL6 in a cell as well as a use of one or more compounds of the application for the preparation of a medicament for inhibiting interactions with BCL6 BTB and/or degrading BCL6 in a cell. The application further includes one or more compounds of the application for use in inhibiting interactions with BCL6 BTB and/or degrading BCL6.

As the compounds of the application have been shown to be capable of inhibiting interactions with BCL6 BTB and degrading BCL6, the compounds of the application are useful for treating diseases, disorders or conditions by inhibiting interactions with BCL6 BTB and/or by degrading BCL6. Therefore the compounds of the present application are useful as medicaments. Accordingly, the present application includes a compound of the application for use as a medicament.

The present application also includes a method of treating a disease, disorder or condition that is treatable by inhibiting interactions with BCL6 BTB and/or by degrading BCL6 comprising administering a therapeutically effective amount of one or more compounds of the application to a subject in need thereof.

The present application also includes a use of one or more compounds of the application for treatment of a disease, disorder or condition that is treatable by inhibiting interactions with BCL6 BTB and/or by degrading BCL6 as well as a use of one or more compounds of the application for the preparation of a medicament for treatment of a disease, disorder or condition that is treatable by inhibiting interactions with BCL6 BTB and/or by degrading BCL6. The application further includes one or more compounds of the application for use in treating a disease, disorder or condition that is treatable by inhibiting interactions with BCL6 BTB and/or by degrading BCL6.

In an embodiment, the disease, disorder or condition is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

Compounds of the application have been demonstrated to inhibit the growth of Karpas422 cells. Therefore in another embodiment of the present application, the disease, disorder or condition that is treatable by inhibiting interactions with BCL6 BTB and/or by degrading BCL6 is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from hematologic cancers, breast cancers, ovarian cancers and glioblastomas. In some embodiments, the cancer is a B-cell lymphoma. In some embodiments, the cancer is a non-Hodgkins lymphoma or a follicular lymphoma. In some embodiments, the cancer is diffuse large B cell lymphoma (DLBCL). In some embodiments, the cancer is a leukemia. In some embodiments, the cancer is BCR-ABL1-positive leukemia. In some embodiments, the cancer is chronic myeloid leukemia (CML) or acute lymphoblastic leukemia (ALL).

In an embodiment, the disease, disorder or condition that is treatable by inhibiting interactions with BCL6 BTB and/or by degrading BCL6 is a disease, disorder or condition associated with an uncontrolled and/or abnormal cellular activity affected directly or indirectly by inhibiting interactions with BCL6 BTB and/or by degrading BCL6. In another embodiment, the uncontrolled and/or abnormal cellular activity that is affected directly or indirectly by inhibiting interactions with BCL6 BTB and/or by degrading BCL6 is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities affected directly or indirectly by inhibiting interactions with BCL6 BTB and/or by degrading BCL6 in a cell, either in a biological sample or in a subject, comprising administering an effective amount of one or more compounds of the application to the cell. The application also includes a use of one or more compounds of the application for inhibition of uncontrolled and/or abnormal cellular activities affected directly or indirectly by inhibiting interactions with BCL6 BTB and/or by degrading BCL6 in a cell as well as a use of one or more compounds of the application for the preparation of a medicament for inhibition of uncontrolled and/or abnormal cellular activities affected directly or indirectly by inhibiting interactions with BCL6 BTB and/or by degrading BCL6 in a cell. The application further includes one or more compounds of the application for use in inhibiting uncontrolled and/or abnormal cellular activities affected directly or indirectly by inhibiting interactions with BCL6 BTB and/or by degrading BCL6 in a cell.

The present application also includes a method of treating a disease, disorder or condition that is treatable by inhibiting interactions with BCL6 BTB and/or by degrading BCL6 comprising administering a therapeutically effective amount of one or more compounds of the application in combination with another known agent useful for treatment of a disease, disorder or condition that is treatable by inhibiting interactions with BCL6 BTB and/or by degrading BCL6 to a subject in need thereof. The present application also includes a use of one or more compounds of the application in combination with another known agent useful for treatment of a disease, disorder or condition that is treatable by inhibiting interactions with BCL6 BTB and/or by degrading BCL6 for treatment of a disease, disorder or condition that is treatable by inhibiting interactions with BCL6 BTB and/or by degrading BCL6, as well as a use of one or more compounds of the application in combination with another known agent useful for treatment of a disease, disorder or condition that is treatable by inhibiting interactions with BCL6 BTB and/or by degrading BCL6 for the preparation of a medicament for treatment of a disease, disorder or condition that is treatable by inhibiting interactions with BCL6 BTB and/or by degrading BCL6. The application further includes one or more compounds of the application in combination with another known agent useful for treatment of a disease, disorder or condition that is treatable by inhibiting interactions with BCL6 BTB and/or by degrading BCL6 for use in treating a disease, disorder or condition that is treatable by inhibiting interactions with BCL6 BTB and/or by degrading BCL6. In an embodiment, the disease, disorder or condition treatable by inhibiting interactions with BCL6 BTB and/or by degrading BCL6 is cancer.

In a further embodiment, the disease, disorder or condition that is treatable by inhibiting interactions with BCL6 BTB and/or by degrading BCL6 is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors therapies, immunotherapy, hormonal therapy and anti-angiogenic therapies.

In some embodiments the interactions that are being inhibited are protein-protein interactions between BCL6 BTB and another protein. In some embodiments, the other protein is a corepressor BCL6 BTB binding protein. In some embodiments the protein is selected from SMRT, NCOR and BCOR.

In some embodiments, the subject is a mammal. In some embodiments, the subject is human.

It will be appreciated by a person skilled in the art that the therapeutic methods and uses of the application would typically comprise administering or use an effective amount of the one or more compounds of the application in a pharmaceutical composition of the application.

IV. Methods of Preparation of Compounds of the Application

Compounds of the present application can be prepared by various synthetic processes. The choice of particular structural features and/or substituents may influence the selection of one process over another. The selection of a particular process to prepare a given compound of Formula I is within the purview of the person of skill in the art. Some starting materials for preparing compounds of the present application are available from commercial chemical sources. Other starting materials, for example as described below, are readily prepared from available precursors using straightforward transformations that are well known in the art.

The compounds of Formula I generally can be prepared according to the processes illustrated in the Schemes below. In the structural formulae shown below the variables are as defined in Formula I unless otherwise stated. A person skilled in the art would appreciate that many of the reactions depicted in the Schemes below would be sensitive to oxygen and water and would know to perform the reaction under an anhydrous, inert atmosphere if needed. Reaction temperatures and times are presented for illustrative purposes only and may be varied to optimize yield as would be understood by a person skilled in the art.

Accordingly in some embodiments, the compounds of Formula I, wherein A is $NCH_3$ are prepared as shown in Scheme 1.

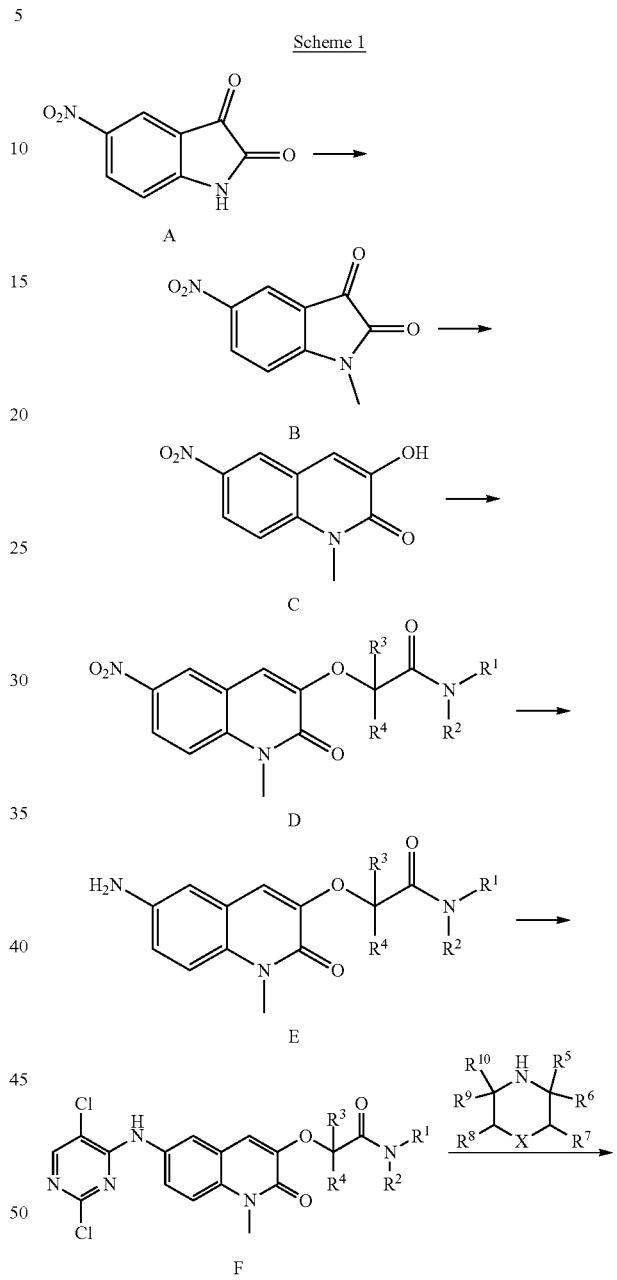

Therefore in some embodiments, compounds A (e.g. commercially available isatins) are methylated under basic conditions to provide compounds B which are subsequently treated with, for example TMS-diazomethane and catalytic amounts of scandium triflates, to provide the ring expanded hydroxyl-quinolone C (see for e.g., Chem Plus Chem 2012, 77, 563-569). Alkylation of C with, for example α-haloacetamides (such as $ClCR^3R^4COR^1R^2$) provides compounds D. Reduction of the nitro group of D, for example under conditions of either Zn/AcOH or Fe/NH4Cl, provides amino intermediate E which upon treatment with 2, 4, 5-trichloropyrimidine provides the advanced intermediate F. Final coupling of F with various cyclic amines provide compounds of Formula I.

In an alternate embodiment, intermediate C may also be prepared from compounds B via ethyldiazoacetate mediated ring expansion to H followed by ester hydrolysis and LiCl-assisted decarboxylation as shown in Scheme 2.

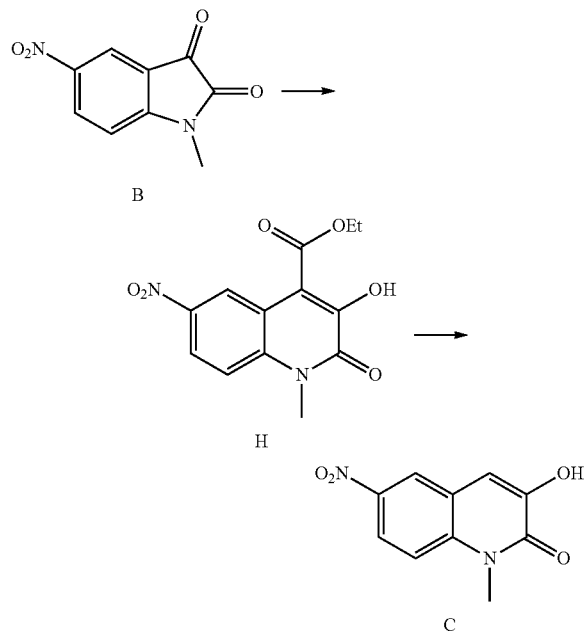

In an alternate embodiment, intermediate E may also be prepared as shown in Scheme 3.

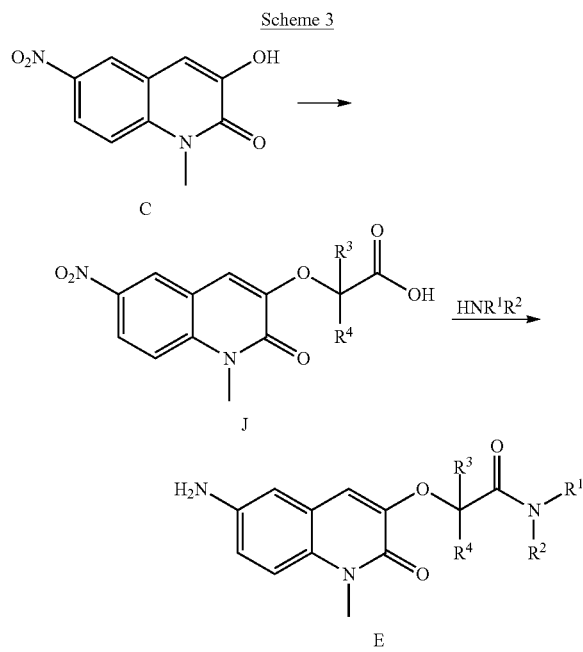

Accordingly intermediates C are alkyled with, for example α-haloacetic acids (e.g ClCR³R⁴COH) providing compound J which are then reacted with various amines (HNR¹R²) to provide intermediates E.

Generally the reactions described above are performed in a suitable inert organic solvent and at temperatures and for times that will optimize the yield of the desired compounds. Examples of suitable inert organic solvents include, but are not limited to, dimethylformamide (DMF), dioxane, methylene chloride, chloroform, tetrahydrofuran (THF), toluene, and the like.

Salts of the compounds of the application are generally formed by dissolving the neutral compound in an inert organic solvent and adding either the desired acid or base and isolating the resulting salt by either filtration or other known means.

The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Prodrugs of the compounds of the present application may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine).

The following non-limiting examples are illustrative of the present application:

EXAMPLES

Example 1: Synthesis and Characterization of Compounds (a) Synthesis of 1-methyl-5-nitroindoline-2,3-dione (1)

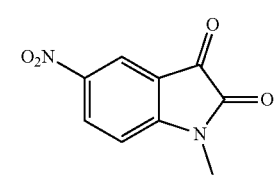

To a solution of 5-nitroisatin (192 mg, 1 mmol) in N,N-dimethylformamide (5 mL) was added potassium carbonate (207 mg, 1.5 mmol) and dimethyl sulfate (0.124 ml g, 1.3 mmol) was added dropwise with stirring. After stirring at room temperature for 2 h, the reaction mixture was poured into ice water (20 mL), and extracted with ethyl acetate (40 mL). The organic layer was dried with sodium sulfate, concentrated, and purified with column chromatography on silica gel (eluting with 0-40% ethyl acetate in hexane) to give 1-methyl-5-nitroindoline-2,3-dione (95 mg, 46% yield) as an orange solid. $^1$H NMR (500 MHz, CHLOROFORM-d) δ=8.53-8.46 (m, 1H), 8.41 (d, J=2.2 Hz, 1H), 6.99 (d, J=8.7 Hz, 1H), 3.30 (s, 4H); LCMS [M+H]$^+$ 207.

(b) Synthesis of 3-hydroxy-1-methyl-6-nitroquinolin-2(1H)-one

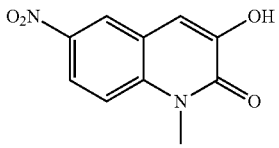 [SMILES: Cn1c(=O)c(O)cc2cc([N+](=O)[O-])ccc21]

Trimethylsilyldiazomethane (1.154 ml, 2M solution in Et₂O, 2.134 mmol) was added to a solution of 1-methyl-5-nitroindoline-2,3-dione (223 mg, 1.082 mmol) and Sc(OTf)₃ (5.86 mg, 0.012 mmol, 11 mol %) in anhydrous dichloromethane (10 mL) cooled at 0° C. The reaction mixture was stirred at RT until the starting material disappeared (as evident by TLC). The solvent was removed under vacuum, and the crude product (238 mg, 100% yield) was used directly in the next step. LCMS [M+H]⁺ 221.

(c) Synthesis of 2-((1-methyl-6-nitro-2-oxo-1,2-dihydroquinolin-3-yl)oxy)acetic-2,2-d2 acid

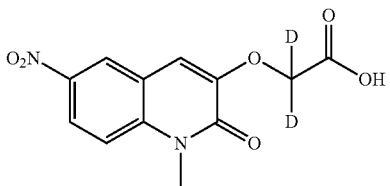 [SMILES: [2H]C([2H])(Oc1cc2cc([N+](=O)[O-])ccc2n(C)c1=O)C(=O)O]

To a solution of 3-hydroxy-1-methyl-6-nitroquinolin-2(1H)-one (250 mg, 1.135 mmol) in acetone (10 ml) was added potassium carbonate (ACS) (314 mg, 2.271 mmol) followed by chloroacetic acid-d3 (221 mg, 2.271 mmol) and sodium iodide (38.3 mg, 0.255 mmol) and heated at 60° C. overnight. LCMS showed complete conversion. The reaction mixture was cooled and concentrated in vacuo. The crude material was neutralized with concentrated HCl to afford 2-((1-methyl-6-nitro-2-oxo-1,2-dihydroquinolin-3-yl)oxy)acetic-2,2-d2 acid (230 mgl, 72% yield) as a beige solid. LCMS [M+1]+ 281

(d) Synthesis of N-(methyl-d3)-2-((1-methyl-6-nitro-2-oxo-1,2-dihydroquinolin-3-yl)oxy)acetamide-2,2-d2

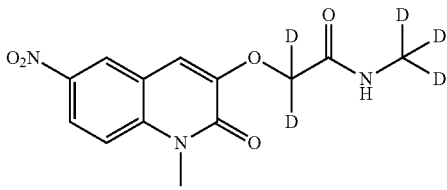

To a solution of 2-((1-methyl-6-nitro-2-oxo-1,2-dihydroquinolin-3-yl)oxy)acetic-2,2-d2 acid (230 mg, 0.821 mmol) in N,N-dimethylformamide (10 mL) was added methylamine hydrochloride (116 mg, 1.641 mmol), HATU (468 mg, 1.231 mmol), and Hunigs base (0.287 ml, 1.641 mmol). The mixture was stirred at room temperature overnight. The reaction was quenched with water (20 mL), and then washed three times with ethyl acetate (20 mL). The combined organics was dried and concentrated. The title compound (235 mg, 97% yield) that was used without further purification. LCMS [M+1]+ 297

(e) Synthesis of N-methyl-2-((1-methyl-6-nitro-2-oxo-1,2-dihydroquinolin-3-yl)oxy)acetamide-2,2-d2

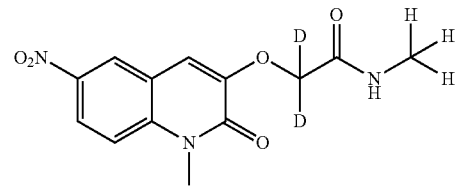

To a solution of 2-((1-methyl-6-nitro-2-oxo-1,2-dihydroquinolin-3-yl)oxy)acetic-2,2-d2 acid (247 mg, 0.881 mmol) in anhydrous N,N-dimethylformamide (DMF) (10 ml) was added methylamine hydrochloride (179 mg, 2.64 mmol), HATU (503 mg, 1.322 mmol) and N,N-diisopropylethylamine (0.461 ml, 2.64 mmol). The mixture was stirred at RT overnight. Additional methylamine hydrochloride (179 mg, 2.64 mmol), HATU (335 mg, 0.881 mmol) and N, N-diisopropylethylamine (0.461 ml, 2.64 mmol) was added. The reaction was stirred at room temperature overnight. Water was added to the reaction and the reaction mixture was filtered to obtain a pale yellow solid. The solid was dried on the high vacuum at RT overnight to afford N-methyl-2-((1-methyl-6-nitro-2-oxo-1,2-dihydroquinolin-3-yl)oxy)acetamide-2,2-d2 (202 mg, 78% yield) as a pale yellow solid. LCMS [M+1]+ 294

(f) Synthesis of 2-((6-amino-1-methyl-2-oxo-1,2-dihydroquinolin-3-yl)oxy)-N-(methyl-d3)acetamide-2,2-d2

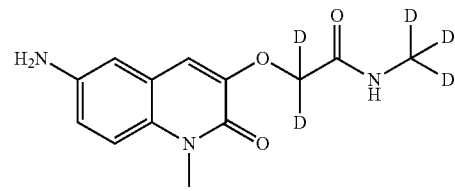 [SMILES: [2H]C([2H])([2H])NC(=O)C([2H])([2H])Oc1cc2cc([N+](=O)[O-])ccc2n(C)c1=O]

To a heterogeneous solution of the N-(methyl-d3)-2-((1-methyl-6-nitro-2-oxo-1,2-dihydroquinolin-3-yl)oxy)acetamide-2,2-d2 (200 mg, 0.675 mmol) in MeOH (6 mL) and AcOH (1.5 mL), was added Zn powder (441 mg, 6.75 mmol) and the reaction mixture was stirred for 30 min. The excess Zn was filtered off and the filtrate was concentrated in vacuo. The residue was washed with satd NaHCO3 (×2), brine (×2), extracted with CH₂Cl₂ and the solvent was removed in vacuo to give 2-(((6-amino-1-methyl-2-oxo-1,2-dihydroquinolin-3-yl)oxy)-N-(methyl-d3)acetamide-2,2-d2 as light brown solid (160 mg, 89% yield) that was used directly in the next step. LCMS [M+1]⁺ 267

(g) Synthesis of 2-((6-amino-1-methyl-2-oxo-1,2-dihydroquinolin-3-yl)oxy)-N-methylacetamide-2,2-d2

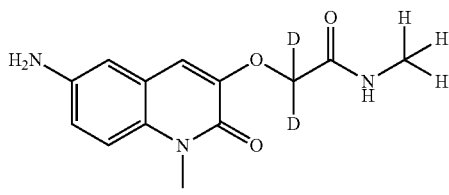 [SMILES: [2H]C([2H])(Oc1cc2cc([N+](=O)[O-])ccc2n(C)c1=O)C(=O)NC]

To a heterogeneous suspension of N-methyl-2-((1-methyl-6-nitro-2-oxo-1,2-dihydroquinolin-3-yl)oxy)acetamide-2,2-d2 (202 mg, 0.689 mmol) in methanol (MeOH) (6.0 ml) and acetic acid (2.000 ml) was added zinc dust (450 mg, 6.89 mmol). The reaction was stirred at RT for 30 min. The suspension was concentrated in vacuo. The solid was taken up in water then basified with saturated NaHCO₃ (aq). The suspension was filtered and the grey solid was dried on the high vacuum pump to afford amino-1-methyl-2-oxo-1,2-dihydroquinolin-3-yl)oxy)-N-methylacetamide-2,2-d2 (181 mg, 100% yield). The crude used in the next step without further purification. LCMS [M+1]⁺ 264

(h) Synthesis of 2-((6-((2,5-dichloropyrimidin-4-yl)amino)-1-methyl-2-oxo-1,2-dihydroquinolin-3-yl)oxy)-N-(methyl-d3)acetamide-2,2-d2

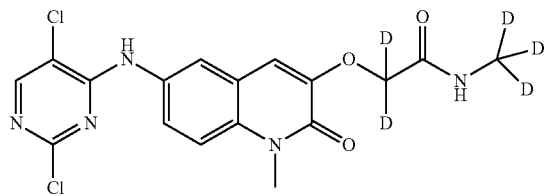 [SMILES: [2H]C([2H])([2H])NC(=O)C([2H])([2H])Oc1cc2cc(Nc3nc(Cl)ncc3Cl)ccc2n(C)c1=O]

The desired 2,4, 5-trichloropyrimidine (132 mg, 0.721 mmol) and DIPEA (0.420 ml, 2.403) were dissolved in IPA (3 ml). The aniline (160 mg, 0.601 mmol) was added and the resulting mixture was refluxed for 1 h. Following cooling, the solvent was removed in vacuo, the residue was triturated with water, filtered and dried under vacuum to afford 2-((6-((2,5-dichloropyrimidin-4-yl)amino)-1-methyl-2-oxo-1,2-dihydroquinolin-3-yl)oxy)-N-(methyl-d3)acetamide-2,2-d2 (208 mg, 84%) as an off-white solid. LCMS [M+1]+ 413

(i) Synthesis of 2-((6-((2,5-dichloropyrimidin-4-yl)amino)-1-methyl-2-oxo-1,2-dihydroquinolin-3-yl)oxy)-N-methylacetamide-2,2-d2

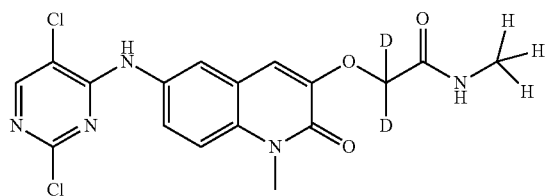 [SMILES: [2H]C([2H])(Oc1cc2cc(Nc3nc(Cl)ncc3Cl)ccc2n(C)c1=O)C(=O)NC]

A reaction vial was charged with 2-((6-amino-1-methyl-2-oxo-1,2-dihydroquinolin-3-yl)oxy)-N-methylacetamide-2,2-d2 (181 mg, 0.687 mmol), N,N-Diisopropylethylamine (0.359 ml, 2.062 mmol) and 2-propanol (2 ml). 2,4,5-Trichloropyrimidine (0.079 ml, 0.687 mmol) was added and the resulting mixture was heated at 80° C. for 1 hour. The suspension was concentrated onto celite and purified on the Biotage (silica gel) eluting with 0-10% MeOH/DCM. The desired fractions were collected, concentrated and dried on the high vacuum pump to afford 2-((6-((2,5-dichloropyrimidin-4-yl)amino)-1-methyl-2-oxo-1,2-dihydroquinolin-3-yl)oxy)-N-methylacetamide-2,2-d2 (204 mg, 72.3% yield) as a pale yellow solid. LCMS [M+1]⁺ 410

(j) Synthesis of 2-((6-((5-chloro-2-((3R,5S)-3,5-dimethylpiperidin-1-yl)pyrimidin-4-yl)amino)-1-methyl-2-oxo-1,2-dihydroquinolin-3-yl)oxy)-N-(methyl-d3)acetamide-2,2-d2 (Example 1a)

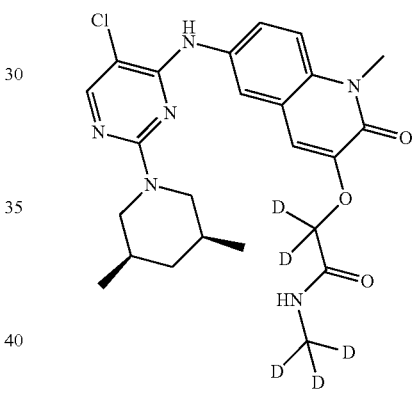

Step 5: 2-((6-((2,5-dichloropyrimidin-4-yl)amino)-1-methyl-2-oxo-1,2-dihydroquinolin-3-yl)oxy)-N-(methyl-d3)acetamide-2,2-d2 (50 mg, 0.121 mmol), Cis 3,5-dimethylpiperidine hydrochloride (217 mg, 1.452 mmol), N,N-diisopropylethylamine (1.0571 mL, 1.84 mmol) in 2-propanol (4 mL) were heated at 150° C. for 30 minutes in a microwave reactor. The reaction mixture was concentrated, triturated with water, and filtered. The residue was washed with ethylacetate and dried to give 2-((6-((5-chloro-2-((3R,5S)-3,5-dimethylpiperidin-1-yl)pyrimidin-4-yl)amino)-1-methyl-2-oxo-1,2-dihydroquinolin-3-yl)oxy)-N-(methyl-d3)acetamide-2,2-d2 (If) as an off-white solid (50 mg, 84%). LCMS [M+H]+ 490; ¹H NMR (500 MHz, DMSO-d6) δ ppm 8.83 (s, 1H), 8.03 (s, 1H), 7.94 (br s, 2H), 7.78-7.69 (m, 1H), 7.47 (br d, J=9.0 Hz, 1H), 7.16 (s, 1H), 4.56-4.42 (m, 2H), 3.68 (s, 3H), 2.28 (br t, J=12.1 Hz, 2H), 1.77 (br d, J=12.3 Hz, 1H), 1.59-1.45 (m, 2H), 0.86 (br d, J=6.1 Hz, 6H).

In a similar manner the following compounds of formula I were synthesized:

| No | Structure | Yields | LCMS & NMR |
|---|---|---|---|
| Ib | 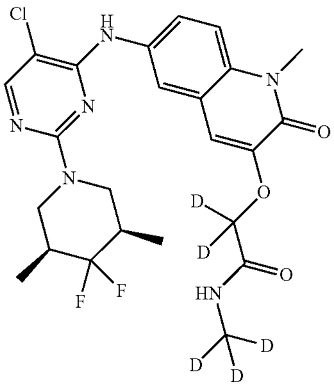 | 51% | ¹H NMR (500 MHz, DMSO-d6) δ ppm 7.95 (s, 1H), 7.69 (d, J = 2.0 Hz, 1H), 7.63 (dd, J = 2.3, 9.0 Hz, 1H), 7.30-7.23 (m, 2H), 6.98 (s, 1H), 6.85 (s, 1H), 4.52 (br d, J = 12.6 Hz, 2H), 3.74 (s, 4H), 2.70 (br t, J = 12.7 Hz, 2H), 1.99-1.82 (m, 2H), 1.61 (s, 5H), 1.01 (d, J = 6.7 Hz, 7H); LCMS [M + H]+ 526. |
| Ih | 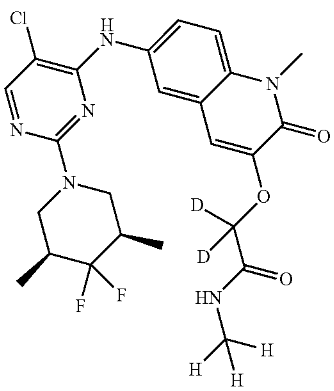 | 94% | 1H NMR (500 MHz, DMSO-d6) δ ppm 8.96 (s, 1 H), 8.08 (s, 1 H), 7.92-7.97 (m, 1 H), 7.89 (d, J = 2.32 Hz, 1 H), 7.70 (dd, J = 9.05, 2.45 Hz, 1 H), 7.47 (d, J = 9.17 Hz, 1 H), 7.19 (s, 1 H), 4.42-4.56 (m, 2 H), 3.68 (s, 3 H), 2.63-2.69 (m, 5 H), 1.97-2.11 (m, 2 H), 0.96 (d, J = 6.60 Hz, 6 H), 19F NMR (471 MHz, DMSO-d6) δ ppm −106.96 (br d, J = 234.09 Hz, 1 F), −132.93 (br d, J = 232.35 Hz, 1 F); LCMS [M + 1]⁺ 524 |
| Ig | 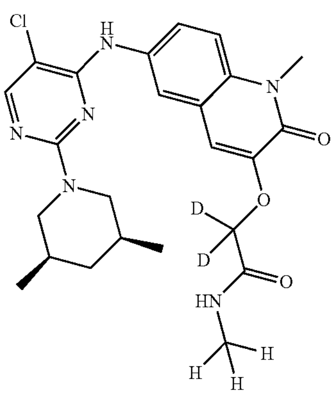 | 87% | ¹H NMR (500 MHz, DMSO-d6) δ ppm 8.82 (s, 1 H), 8.03 (s, 1 H), 7.93 (d, J = 2.32 Hz, 2 H), 7.73 (dd, J = 9.11, 2.38 Hz, 1 H), 7.46 (d, J = 9.17 Hz, 1H), 7.15 (s, 1 H), 4.48 (br d, J = 10.15 Hz, 2 H), 3.68 (s, 3 H), 2.66 (d, J = 4.77 Hz, 3 H), 2.27 (t, J = 12.10 Hz, 2 H), 1.77 (br d, J = 12.84 Hz, 1 H), 1.48-1.57 (m, 2 H), 0.85 (d, J = 6.60 Hz, 6 H), 0.81 (br dd, J = 4.03, 2.20 Hz, 1 H); LCMS [M + 1]⁺ 487 |

(k) Synthesis of ethyl 3-hydroxy-1-methyl-6-nitro-2-oxo-1,2-dihydroquinoline-4-carboxylate

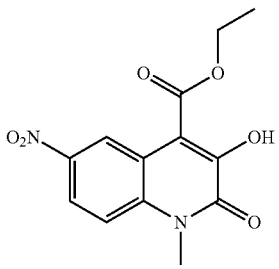 [SMILES: CCOC(=O)c1c(O)c(=O)n(C)c2ccc([N+](=O)[O-])cc12]

To a solution of 1-methyl-5-nitroindoline-2,3-dione (533 mg, 2.59 mmol) in absolute ethanol (EtOH) (5 ml) at 0° C., was added diethylamine (0.508 ml, 4.91 mmol) followed by ethyldiazoacetate solution (4.18 ml, 4.91 mmol) dropwise. The reaction was allowed to stir overnight at RT. The mixture was evaporated to remove the EtOH and 1N HCl (ca. 50 mL) was added. The mixture was then left to stir for 3 hr. The precipitate was filtered, rinsed with water (2×) and dried under vacuum to give ethyl 3-hydroxy-1-methyl-6-nitro-2-oxo-1,2-dihydroquinoline-4-carboxylate (1.858 mmol, 71.9% yield) as an orange solid. $^1$H NMR (500 MHz, DMSO-d6) δ=10.96 (br s, 1H), 8.33 (d, J=2.6 Hz, 1H), 8.27 (dd, J=2.6, 9.3 Hz, 1H), 7.77 (d, J=9.3 Hz, 1H), 4.45 (q, J=7.1 Hz, 2H), 3.77 (s, 3H), 1.35 (t, J=7.1 Hz, 3H) LCMS [M+1]+ 293.5.

(l) Alternative synthesis of 3-hydroxy-1-methyl-6-nitroquinolin-2(1H)-one

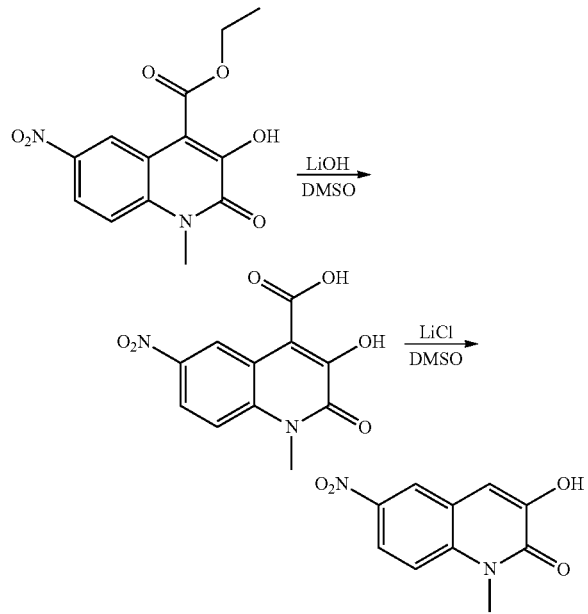

Ethyl 3-hydroxy-1-methyl-6-nitro-2-oxo-1,2-dihydroquinoline-4-carboxylate (22 g, 75.2 mmol, 1 eq) in DMSO (752 ml) was treated with H$_2$O (75 ml) followed by LiOH (3 eq) at 120-130° C. for 16 h, TLC analysis indicated formation of polar spot. The reaction was neutralized with 1N HCl. The reaction was concentrated to reveal a solid which was filtered and washed with water (2×). The solid was dried on the under vacuum to obtain 3-hydroxy-1-methyl-6-nitro-2-oxo-1,2-dihydroquinoline-4-carboxylic acid (14 g, 71% yield) as a black solid.

3-Hydroxy-1-methyl-6-nitro-2-oxo-1,2-dihydroquinoline-4-carboxylic acid (14 g, 53 mmol, 1 eq) in DMSO (10 v) was treated with H$_2$O (1 v) followed by LiCl (3 eq) at 120-130° C. for 5 h. TLC analysis indicated formation of less polar spot. Work-up and purification gave 9 g (78% yield) of 3-hydroxy-1-methyl-6-nitroquinolin-2(1H)-one as a beige solid.

Example 2: Biological Assays

Compounds of the present application displayed inhibition of the interaction between BCL6-BTB domain and SMRT/NCOR2 in the following assays:

(a) BCL6-BTB—SMRT Peptide Inhibition Fluorescence Polarization (FP) Screen

This assay is used to determine whether compounds inhibit the interaction between the BTB domain of BCL6 and a peptide derived from the BCL6 binding domain (BBD) of the SMRT/NCOR2 corepressor protein Compounds were dissolved in 100% DMSO at 10 mM, assayed fresh, and then stored at −20° C. for repeat studies and future work. The reaction mixture consists of 1.25 uM of the 25 kd BCL6-BTB domain (Thioredoxin-His6-STag-TEV-biotinylation-thrombin-BCL6 amino acids 1-129) plus 20 nM of the peptide probe Ac-GSLVATVKEAGRSIHEIPA (SEQ ID NO: 1) with 16 amino acid peptide from the SMRT BBD (1414-1429) with a Bodipy-TMR fluorescent label on the lysine. The assay buffer was 10 mM HEPES pH7.4, 150 mM NaCl, 0.05% Tween-20, 3 mM EDTA, and had a final DMSO concentration of 5%. 20 ul of this assay mixture was added to each well of the 384 well plates with the exception of the control wells that contained no protein (for setting the minimum FP value). Compounds were directly sprayed using an HP D300 Digital Dispenser from 10 mM DMSO stocks onto black 384 well plates (greiner bio-one #781900) in a concentration range from 1 uM to 500 uM (10 points in duplicate). The assay was equilibrated for 1 hour prior to reading the FP values (Ex 540 nm/Em 580 nm) with a Perkin Elmer Envision plate reader. The results were curve fitted and IC$_{50}$ values were calculated using the BioAssay software from CambridgeSoft. Representative compounds displayed IC$^{50}$<1 uM in this assay (NB: lower limit of this assay was 1 uM).

(b) Surface Plasmon Resonance (SPR) Assay

SPR studies were performed using a Biacore™ T200 instrument (GE Health Sciences Inc.). The BCL6 BTB protein used in the FP assay was biotinylated using the site specific biotinylating enzyme BirA, and then cleaved with TEV protease to produce the BCL6 BTB domain (biotin-thrombin-BCL6 amino acids 1-129; 17 kd) that was use in SPR. This protein was stably captured (1000RU) to streptavidin coupled SA chips (BR-1005-31, GE Health Sciences Inc.) according to the manufacture's protocol. Compounds were dissolved in 100% DMSO at 10 mM and 2-fold serial dilutions were done in 100% DMSO. For SPR analysis the serially titrated compounds were diluted 1/20 into buffer (10 mM HEPES pH7.4, 150 mM NaCl, 0.05% Tween-20, 3 mM EDTA) giving a final concentration of 5% DMSO. The Biacore flow rate was set at 100 ul/min. For $K_D$ determinations, single cycle kinetic analysis was performed with an on time of 60 seconds, and an off time of 300 seconds. Curve fitting and KD calculations were done with the Biacore T200 Evaluation software (GE Health Sciences Inc). Results are presented in Table 1.

(c) Cell-Based Luciferase Assay:

A BCL6 reporter construct containing three copies of the consensus BCL6 binding site, the TK promoter, and the firefly luciferase gene was stably expressed in SuDHL4 cells after lentivirus infection and selection with Blasticidin. SuDHL4-3×BCL6-TK-Luc cells were seeded into a Viewplate 384-well assay dish at 15,000 cells/well in 25 ul medium (Alpha-MEM high glucose containing 10% FBS, 25 mM HEPES, 200 mM GlutaMAX, 100 ug/ml Normocin, and 50 mg/ml Gentamycin, Invitrogen). A HP D300 digital dispenser was used to dose cells with DMSO or test compounds across a 10-point range of concentrations (high dose of 10 uM), and cultures were grown in a humidified 5% $CO_2$ incubator at 37° C. After two days, plates were removed from incubator and equilibrated to room temperature. An equal volume of neolite reporter gene assay reagent was added to each well, and samples were processed according to manufacturer's instructions (Perkin Elmer). Luminescent signal was measured using an Envision plate reader equipped with a US-Luminescence detector. Results are presented in Table 1.

(d) Tumor Cell Growth inhibition Assay:

Karpas422 cells were seeded into a 96-well plate at 2,000 cells/well in 150 ul medium (Alpha-MEM containing 10% FBS, 100 mg/ml Normocin, and 50 mg/ml Gentamycin, Invitrogen). A HP D300 digital dispenser was used to dose cells with DMSO or test compounds across a 10-point range of concentrations (high dose of 5 uM), and cultures were grown in a humidified 5% $CO_2$ incubator at 37° C. After six days, plates were removed from incubator and equilibrated to room temperature. An equal volume of ATPlite assay reagent was added to each well, and samples were processed according to manufacturer's instructions (Perkin Elmer). Luminescent signal was measured using an Envision plate reader equipped with a US-Luminescence detector. Results are presented in Table 1.

(e) BCL6 Degradation Assays $1\times10^6$ Karpas422 cells were treated with example, positive and negative control compounds at a concentration of 1 μM for 1 h at 37° C., in complete culture medium ((α-MEM supplemented 10% FBS). Cells were harvested via centrifugation, rinsed with cold DPBS, and lysed with modified RIPA buffer (+1% SDS). Total protein extracts were quantified using the Bio Rad DC assay, and 1.5 μg total protein was run on the WES capillary electrophoresis system. Antibodies for BCL6 and β-actin were used to probe for protein expression levels within each capillary. BCL6 expression levels were normalized to intra-capillary @-actin, and expressed as fold BCL6 protein relative to DMSO. Results are presented in FIG. 1.

(f) Microsomal Stability Assays

Liver Microsomal Metabolic Stability

In Phase I analysis test compounds were incubated at a final concentration of 1 μM (this concentration was assumed to be well below the Km values to ensure linear reaction conditions i.e. to avoid saturation). Working stocks were initially diluted to a concentration of 40.0 μM in 0.1 M potassium phosphate buffer (pH 7.4) before addition to the reaction vials. CD-1 mouse (male) or pooled human liver microsomes (Corning Gentest) were utilized at a final concentration of 0.5 mg/mL (protein). Duplicate wells were used for each time point (0 and 60 minutes). Reactions were carried out at 37° C. in an orbital shaker at 175 rpm, and the final DMSO concentration was kept constant at 0.1%. The final volume for each reaction was 100 μL, which includes the addition of an NADPH-Regeneration Solution (NRS) mix. This NRS mix is comprised of glucose 6-phosphate dehydrogenase, NADP+, $MgCl_2$, and glucose 6-phosphate. Upon completion of the 60 minute time point, reactions were terminated by the addition of 2-volumes (200 μL) of ice-cold, acetonitrile containing 0.5% formic acid and internal standard. Samples were then centrifuged at 4,000 rpm for 10 minutes to remove debris and precipitated protein. Approximately 150 μL of supernatant was subsequently transferred to a new 96 well microplate for LC/MS analysis:

Narrow-window mass extraction LC-MS analysis was performed for all samples in this study using a Waters Xevo quadrupole time-of-flight (QTof) mass spectrometer to determine relative peak areas of test compounds. The percent remaining values are calculated using the following equations:

$$\% \text{ remaining} = (A)/A_0 \times 100$$

where

A is area response after incubation $A_0$ is area response at initial time point For intrinsic clearance assay, incubation mixtures contained probe substrate, liver microsomes and an NADPH regenerating system (1.3 mM NADP+, 3.3 mM glucose 6-phosphate, 0.4 U ml$^{-1}$ glucose 6-phosphate dehydrogenase, 3.3 mM magnesium chloride) in 0.1 M potassium phosphate buffer (pH 7.4). CD-1 mouse (male) or pooled human liver microsomes (Corning Gentest) were utilized at a final concentration of 0.5 mg/mL (protein). 12.5 μL of each drug solution were placed into a well of 96 well plate. Reactions were initiated by the addition of activated microsome solutions (500 μL) to drug solutions. Reactions were carried out at 37° C. in an orbital shaker at 175 rpm, and the final DMSO concentration was kept constant at 0.1%. Test compounds were incubated at a final concentration of 1 μM. 50 μL of aliquots of reaction mixtures were quenched by mixing with two parts of stop solution (internal standard containing 0.5% formic acid in acetonitrile) at appropriate time-points and mixed well. Then, solutions were centrifuged at 4000 rpm for 10 min. Supernatants were transferred to a new 96-well plate and analyzed by a Waters Q-TOF mass spectrometer coupled with an UPLC System. Recovery analysis was performed using relative peak areas and narrow window mass extraction.

The ln(% remaining) is plotted against time and the gradient of the line determined.

Elimination Constant ($k$)=−slope

Half-life ($t^{1/2}$)(min)=ln $2/k$=0.693/$k$ $V$ (μL/mg)=volume of incubation (μL)/protein in the incubation (mg)

Intrinsic Clearance ($CL_{int}$)(μL/min/mg protein)= $V \cdot 0.693/t^{1/2} = V \cdot k$ The metabolic stability (human and mouse) and intrinsic clearance properties of representative compounds of the application showing significantly improved metabolic stability profiles relative to BI-3802 are presented in Table 2.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Tumour Cell Growth Inhibition Assay Results

| Example # | FP uM | SPR $K_d$ uM | Luc IC$_{50}$ uM | GI Karpas EC$_{50}$ uM |
|---|---|---|---|---|
| Ia | 1.0 | 0.00456 | 0.0466 | 0.0141 |
| Ib | 0.9 | 0.00453 | 0.00757 | 0.00504 |

TABLE 2

Metabolic Stability and Clearance Properties

| Example # | Human Liver Microsomes (HLM, % @ 1 h) | Mouse Liver Microsomes (MLM, % @ 1 h) | $T_{1/2}$ (min) | Clint (μL/min/mg protein) |
|---|---|---|---|---|
| BI-3802 | 25 | 13 | 12 | 112 |
| Ia | 26 | 8 | 29 | 48 |
| Ib | 100 | 91 | 82 | 17 |

The invention claimed is:

1. A compound of formula I, or a pharmaceutically acceptable salt, thereof:

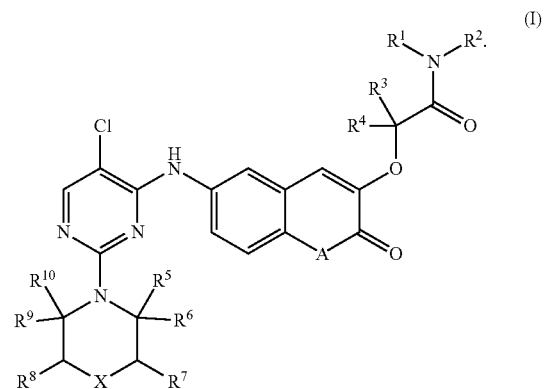

A is selected from O and NR$^{11}$;

X is selected from CH$_2$, CF$_2$, CD$_2$, CHF, CDF and CHD;

R$^1$ and R$^2$ are independently selected from H, D, C$_{1-4}$alkyl and deuterium-substituted C$_{1-4}$alkyl;

R$^3$, R$^4$, R$^5$, R$^6$, R$^9$ and R$^{10}$ are independently selected from H and D;

R$^7$ and R$^8$ are independently CR$^{12}$R$^{13}$R$^{14}$,

R$^{11}$ is selected from H, C$_{1-4}$alkyl and deuterium-substituted C$_{1-4}$alkyl;

R$^{12}$, R$^{13}$ and R$^{14}$ are independently selected from H, D and F; and all alkyl groups are optionally fluoro-substituted and the compound of Formula I comprises at least one D.

2. The compound of claim 1, wherein A is NR$^{11}$ and R$^{11}$ is selected from H, CH$_3$ and CD$_3$.

3. The compound of claim 2, wherein A is NCH$_3$.

4. The compound of claim 1, wherein X is selected from CH$_2$, and CF$_2$.

5. The compound of claim 1, wherein R$^1$ and R$^2$ are independently selected from CH$_3$ and CD$_3$.

6. The compound of claim 1, wherein R$^3$, R$^4$, R$^5$, R$^6$, R$^9$ and R$^{10}$ are all H, or R$^3$, R$^4$, R$^5$, R$^6$, R$^9$ and R$^{10}$ are all D.

7. The compound of claim 1, wherein R$^3$ and R$^4$ are D and R$^5$, R$^6$, R$^9$ and R$^{10}$ are all H.

8. The compound of claim 1, wherein R$^7$ and R$^8$ are the same and are selected from CH$_3$, CF$_3$, CD$_3$ and CD$_2$F.

SEQUENCE LISTING

```
<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Synthetic construct

<400> SEQUENCE: 1

Gly Ser Leu Val Ala Thr Val Lys Glu Ala Gly Arg Ser Ile His Glu
1               5                   10                  15

Ile Pro Ala
```

9. The compound of claim 1, wherein the stereochemistry in the compounds of Formula I is as follows:
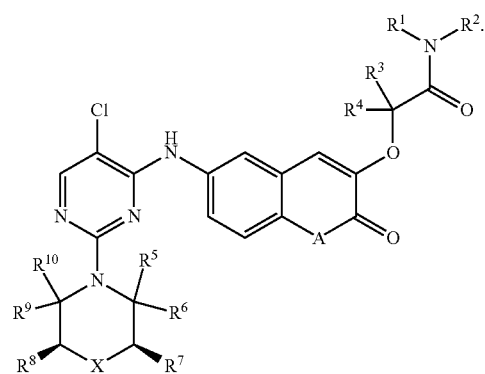
10. The compound of claim 1 selected from:
| No | Structure |
|---|---|
| Ia | (structure) |
| Ib | (structure) |
| Ic | (structure) |
| Ie | (structure) |
| If | (structure) |
| Ig | (structure) |

| No | Structure |
|---|---|
| Ih | (structure) |
| Ii | (structure) |
| Ij | (structure) |
| Ik | (structure) |
| Il | (structure) |
| Im | (structure) |
| In | (structure) |
| Io | (structure) |

-continued

| No | Structure |
|---|---|
| Ip | (structure) |
| Iq | (structure) |
| Ir | (structure) |
| Is | (structure) |
| It | (structure) |
| Iu | (structure) |
| Iv | (structure) |
| Iw | (structure), and |

| No | Structure |
|---|---|
| Ix | [chemical structure] | or a pharmaceutically acceptable salt thereof.

11. The compound of claim 1, selected from:

| No | Structure |
|---|---|
| Ia | [chemical structure] |
| Ib | [chemical structure] |
| Ih | [chemical structure] |
| Ig | [chemical structure] | or a pharmaceutically acceptable salt thereof.

12. A pharmaceutical composition comprising one of more compounds of claim 1 and a pharmaceutically acceptable carrier.

13. A method for inhibiting interactions with BCL6 BTB and/or degrading BCL6 in a cell, comprising administering an effective amount of one or more compounds of claim 1 to the cell.

14. A method of treating a lymphoma comprising administering a therapeutically effective amount of one or more compounds of claim 1 to a subject in need thereof.

15. The method of claim 14, wherein the lymphoma is a B-cell lymphoma, a non-Hodgkins lymphoma, or a follicular lymphoma.

16. The method of claim 14, wherein the lymphoma is diffuse large B cell lymphoma (DLBCL).

* * * * *

UNITED STATES PATENT AND TRADEMARK OFFICE
CERTIFICATE OF CORRECTION

| | |
|---|---|
| PATENT NO. | : 11,505,539 B2 |
| APPLICATION NO. | : 16/955998 |
| DATED | : November 22, 2022 |
| INVENTOR(S) | : Methvin Isaac, Anh My Chau and Ahmed Mamai |

It is certified that error appears in the above-identified patent and that said Letters Patent is hereby corrected as shown below:

In the Claims

Claim 12, Column 54, Line 37, "A pharmaceutical composition comprising one of" should read -- A pharmaceutical composition comprising one or --.

Signed and Sealed this
Twentieth Day of February, 2024

Katherine Kelly Vidal
*Director of the United States Patent and Trademark Office*